United States Patent
Olsen et al.

(10) Patent No.: US 12,285,564 B2
(45) Date of Patent: *Apr. 29, 2025

(54) HEADGEAR CLIP ARRANGEMENT

(71) Applicant: Fisher & Paykel Healthcare Limited, Auckland (NZ)

(72) Inventors: Gregory James Olsen, Auckland (NZ); Hamish Joshua Rose, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 725 days.

This patent is subject to a terminal disclaimer.

(21) Appl. No.: 17/302,586

(22) Filed: May 6, 2021

(65) Prior Publication Data
US 2021/0252244 A1    Aug. 19, 2021

Related U.S. Application Data

(63) Continuation of application No. 15/325,982, filed as application No. PCT/IB2015/055412 on Jul. 17, 2015, now Pat. No. 11,027,087.

(Continued)

(51) Int. Cl.
*A61M 16/06* (2006.01)

(52) U.S. Cl.
CPC ... *A61M 16/0683* (2013.01); *A61M 2205/586* (2013.01)

(58) Field of Classification Search
CPC ..... A44B 13/02; A44B 13/0017; A44B 11/28; A44B 13/0025; A44B 13/0035;

(Continued)

(56) References Cited

U.S. PATENT DOCUMENTS

| 301,111 A | 7/1884 | Genese |
| 472,238 A | 4/1892 | Van Orden |

(Continued)

FOREIGN PATENT DOCUMENTS

| AU | 744593 | 2/2002 |
| AU | 2003246441 | 12/2003 |

(Continued)

OTHER PUBLICATIONS

U.S. Appl. No. 60/842,741, filed Sep. 7, 2006, Ho et al.

(Continued)

*Primary Examiner* — Timothy A Stains
*Assistant Examiner* — Tina Zhang
(74) *Attorney, Agent, or Firm* — VIA LLP

(57) ABSTRACT

A headgear connection assembly for a respiratory mask is configured to provide easy use and a reliable connection. The headgear connection assembly may include a clip attachment portion and a clip. The clip may include a hook, a headgear attachment loop, and one or more finger grips. The hook may be configured to include a central portion and two outer portions and an interference bump and to engage with a post of the clip attachment portion. The central and outer portions of the hook may be configured to flex independently of one another. The clip attachment portion may include geometry to limit rotation of the clip.

14 Claims, 14 Drawing Sheets

Related U.S. Application Data

(60) Provisional application No. 62/026,452, filed on Jul. 18, 2014.

(58) Field of Classification Search
CPC . A44B 13/0041; A44B 13/0052; A44B 11/00; A61M 16/0683; A61M 16/0694; A61M 16/06; A61M 2205/586; A61M 2205/582; A61F 9/027; A61F 2007/0228; F16G 11/143; F16G 11/146; A41D 13/1161
See application file for complete search history.

(56) References Cited

U.S. PATENT DOCUMENTS

| | | | |
|---|---|---|---|
| 558,616 A * | 4/1896 | Schoeppl | A44B 17/007 24/698.2 |
| 577,926 A | 3/1897 | Miller | |
| 581,921 A * | 5/1897 | Shoeppl | A44B 13/0011 24/697.2 |
| 687,973 A | 12/1901 | Bohn | |
| 717,485 A * | 12/1902 | Wolfbauer | A44B 13/0047 24/698.2 |
| 718,470 A | 1/1903 | Jones | |
| 751,091 A | 2/1904 | Moran | |
| 770,013 A | 9/1904 | Linn | |
| 954,458 A | 4/1910 | Patterson | |
| 1,439,168 A * | 12/1922 | Hongler | A44B 13/02 24/697.2 |
| 1,635,545 A | 7/1927 | Drager | |
| 1,674,894 A * | 6/1928 | Engle | A44B 13/0017 24/363 |
| 1,795,619 A * | 3/1931 | Roseman | A44B 13/0052 24/698.3 |
| 2,157,037 A * | 5/1939 | Troendly | A44B 11/28 24/321 |
| 2,228,218 A | 1/1941 | Schwartz | |
| 2,296,150 A | 9/1942 | Dockson et al. | |
| 2,359,506 A | 10/1944 | Battley et al. | |
| 2,376,871 A | 5/1945 | Fink | |
| 2,388,604 A | 11/1945 | Eisenbud | |
| 2,508,050 A | 5/1950 | Valente | |
| 2,693,800 A | 11/1954 | Caldwell | |
| 2,706,983 A | 4/1955 | Matheson et al. | |
| 2,738,788 A | 3/1956 | Matheson et al. | |
| 2,843,121 A | 7/1958 | Hudson | |
| 2,858,828 A | 11/1958 | Matheson | |
| 2,859,748 A | 11/1958 | Hudson | |
| 2,874,693 A | 2/1959 | Matheson | |
| 2,881,444 A | 4/1959 | Fresh et al. | |
| 2,893,387 A | 7/1959 | Gongoll et al. | |
| 2,939,458 A | 6/1960 | Lundquist | |
| 2,999,498 A | 9/1961 | Matheson | |
| 3,037,501 A | 6/1962 | Miller | |
| 3,162,919 A * | 12/1964 | Shee | A44B 13/0017 24/698.2 |
| 3,424,633 A | 1/1969 | Corrigall et al. | |
| 3,490,452 A | 1/1970 | Greenfield | |
| 3,827,716 A * | 8/1974 | Vaughn | B60R 22/14 24/698.2 |
| 3,850,171 A | 11/1974 | Ball et al. | |
| 3,890,966 A | 6/1975 | Aspelin et al. | |
| 3,936,914 A | 2/1976 | Mancini | |
| 3,972,321 A | 8/1976 | Proctor | |
| 3,977,432 A | 8/1976 | Vidal | |
| 3,982,532 A | 9/1976 | Halldin et al. | |
| 3,992,720 A | 11/1976 | Nicolinas | |
| 4,010,501 A * | 3/1977 | Cooke | A44B 11/28 441/118 |
| 4,027,360 A * | 6/1977 | Moser | B60J 7/104 24/713.3 |
| 4,040,501 A | 8/1977 | Haswell | |
| 4,054,972 A * | 10/1977 | Rowell | A41C 3/02 24/698.2 |
| 4,069,516 A | 1/1978 | Watkins, Jr. | |
| 4,090,510 A | 5/1978 | Segersten | |
| 4,141,118 A | 2/1979 | Gudell | |
| 4,201,205 A | 5/1980 | Bartholomew | |
| 4,258,710 A | 3/1981 | Reber | |
| 4,266,540 A | 5/1981 | Panzik et al. | |
| 4,278,082 A | 7/1981 | Blackmer | |
| 4,354,488 A | 10/1982 | Bartos | |
| 4,367,735 A | 1/1983 | Dali | |
| 4,378,011 A | 3/1983 | Warncke et al. | |
| 4,437,462 A | 3/1984 | Piljay | |
| 4,466,159 A | 8/1984 | Burrage | |
| 4,676,241 A | 6/1987 | Webb et al. | |
| 4,706,683 A | 11/1987 | Chilton et al. | |
| 4,739,755 A | 4/1988 | White et al. | |
| 4,753,233 A | 6/1988 | Grimes | |
| 4,782,832 A | 11/1988 | Trimble et al. | |
| 4,836,200 A | 6/1989 | Clark et al. | |
| 4,856,508 A | 8/1989 | Tayebi | |
| 4,915,104 A | 4/1990 | Marcy | |
| 4,915,105 A | 4/1990 | Lee | |
| 4,919,128 A | 4/1990 | Kopala et al. | |
| 4,938,209 A | 7/1990 | Fry | |
| 4,941,467 A | 7/1990 | Takata | |
| 4,944,310 A | 7/1990 | Sullivan | |
| 4,971,051 A | 11/1990 | Toffolon | |
| 4,974,586 A | 12/1990 | Wandel et al. | |
| 4,986,269 A | 1/1991 | Hakkinen | |
| 5,010,925 A | 4/1991 | Atkinson et al. | |
| 5,016,625 A | 5/1991 | Hsu et al. | |
| 5,031,261 A | 7/1991 | Fenner | |
| 5,042,478 A | 8/1991 | Kopala et al. | |
| 5,062,421 A | 11/1991 | Burns et al. | |
| 5,065,756 A | 11/1991 | Rapoport | |
| 5,074,297 A | 12/1991 | Venegas | |
| 5,094,236 A | 3/1992 | Tayebi | |
| 5,113,857 A | 5/1992 | Dickerman et al. | |
| 5,120,300 A | 6/1992 | Shaw | |
| 5,148,802 A | 9/1992 | Sanders et al. | |
| 5,164,652 A | 11/1992 | Johnson et al. | |
| 5,231,979 A | 8/1993 | Rose et al. | |
| 5,243,971 A | 9/1993 | Sullivan et al. | |
| 5,245,995 A | 9/1993 | Sullivan et al. | |
| 5,259,377 A | 11/1993 | Schroeder | |
| 5,269,296 A | 12/1993 | Landis | |
| 5,349,949 A | 9/1994 | Schegerin | |
| 5,353,789 A | 10/1994 | Schlobohm | |
| 5,355,878 A | 10/1994 | Griffiths et al. | |
| 5,377,394 A * | 1/1995 | Fildan | A44B 11/2588 24/616 |
| 5,400,776 A | 3/1995 | Bartholomew | |
| 5,429,683 A | 7/1995 | Le Mitouard | |
| 5,438,981 A | 8/1995 | Starr et al. | |
| 5,441,046 A | 8/1995 | Starr et al. | |
| 5,449,206 A | 9/1995 | Lockwood | |
| 5,449,234 A | 9/1995 | Gipp et al. | |
| 5,477,852 A | 12/1995 | Landis et al. | |
| 5,513,634 A | 5/1996 | Jackson | |
| 5,518,802 A | 5/1996 | Colvin et al. | |
| 5,533,506 A | 7/1996 | Wood | |
| 5,540,223 A | 7/1996 | Starr et al. | |
| 5,542,128 A | 8/1996 | Lomas | |
| 5,551,419 A | 9/1996 | Froehlich et al. | |
| 5,558,090 A | 9/1996 | James | |
| 5,570,689 A | 11/1996 | Starr | |
| 5,588,423 A | 12/1996 | Smith | |
| 5,595,174 A | 1/1997 | Gwaltney | |
| 5,601,078 A | 2/1997 | Schaller et al. | |
| 5,647,355 A | 7/1997 | Starr et al. | |
| 5,649,532 A | 7/1997 | Griffiths | |
| 5,657,752 A | 8/1997 | Landis et al. | |
| D383,204 S | 9/1997 | Lomas | |
| 5,662,101 A | 9/1997 | Ogden et al. | |
| 5,664,566 A | 9/1997 | Mcdonald et al. | |
| 5,690,097 A | 11/1997 | Howard et al. | |
| 5,724,965 A | 3/1998 | Handke et al. | |
| 5,746,201 A | 5/1998 | Kidd | |
| 5,752,510 A | 5/1998 | Goldstein | |
| 5,755,578 A | 5/1998 | Contant et al. | |
| 5,758,642 A | 6/1998 | Choi | |

(56) References Cited

U.S. PATENT DOCUMENTS

| | | |
|---|---|---|
| 5,806,727 A | 9/1998 | Joseph |
| 5,826,313 A * | 10/1998 | Ishizaki ............ A44B 13/0023 |
| | | 24/698.2 |
| 5,842,470 A | 12/1998 | Ruben |
| 5,857,460 A | 1/1999 | Popitz |
| 5,878,743 A | 3/1999 | Zdrojkowski et al. |
| 5,884,624 A | 3/1999 | Barnett et al. |
| 5,896,857 A | 4/1999 | Hely et al. |
| 5,904,278 A | 5/1999 | Barlow et al. |
| 5,906,033 A | 5/1999 | Mukaiyama |
| 5,921,239 A | 7/1999 | McCall et al. |
| 5,937,851 A | 8/1999 | Serowski et al. |
| 5,941,245 A | 8/1999 | Hannah et al. |
| 5,943,473 A | 8/1999 | Levine |
| 5,953,763 A | 9/1999 | Gouget |
| 5,975,079 A * | 11/1999 | Hellings ............... A61M 16/06 |
| | | 128/206.28 |
| 6,006,748 A | 12/1999 | Hollis |
| 6,016,804 A | 1/2000 | Gleason et al. |
| 6,017,315 A | 1/2000 | Starr et al. |
| 6,019,101 A | 2/2000 | Cotner et al. |
| 6,039,044 A | 3/2000 | Sullivan |
| 6,050,260 A | 4/2000 | Daniell et al. |
| 6,050,294 A | 4/2000 | Makowan |
| 6,112,746 A | 9/2000 | Kwok et al. |
| 6,116,235 A | 9/2000 | Walters et al. |
| 6,119,693 A | 9/2000 | Kwok et al. |
| 6,119,694 A | 9/2000 | Correa et al. |
| 6,135,432 A | 10/2000 | Hebblewhite et al. |
| 6,192,886 B1 | 2/2001 | Rudolph |
| 6,269,814 B1 | 8/2001 | Blaszczykiewicz et al. |
| 6,272,933 B1 | 8/2001 | Gradon et al. |
| 6,298,850 B1 | 10/2001 | Argraves |
| 6,302,105 B1 | 10/2001 | Wickham et al. |
| 6,341,606 B1 | 1/2002 | Bordewick et al. |
| 6,347,631 B1 | 2/2002 | Hansen et al. |
| 6,355,878 B1 | 3/2002 | Kim et al. |
| 6,398,197 B1 | 6/2002 | Dickinson et al. |
| 6,412,488 B1 | 7/2002 | Barnett et al. |
| 6,418,928 B1 | 7/2002 | Bordewick et al. |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,457,473 B1 | 10/2002 | Brostrom et al. |
| 6,460,539 B1 | 10/2002 | Japuntich et al. |
| 6,467,483 B1 | 10/2002 | Kopacko et al. |
| 6,478,026 B1 | 11/2002 | Wood |
| 6,484,725 B1 | 11/2002 | Chi et al. |
| 6,488,664 B1 | 12/2002 | Solomon et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,557,555 B1 | 5/2003 | Hollis |
| 6,561,188 B1 | 5/2003 | Ellis |
| 6,561,190 B1 | 5/2003 | Kwok |
| 6,561,191 B1 | 5/2003 | Kwok |
| 6,581,594 B1 | 6/2003 | Drew et al. |
| 6,581,601 B2 | 6/2003 | Ziaee |
| 6,581,602 B1 | 6/2003 | Kwok et al. |
| 6,584,977 B1 | 7/2003 | Serowski |
| 6,588,424 B2 | 7/2003 | Bardel |
| 6,595,214 B1 | 7/2003 | Hecker |
| 6,615,832 B1 | 9/2003 | Chen |
| 6,631,718 B1 | 10/2003 | Lovell |
| 6,634,357 B1 | 10/2003 | Hamilton |
| 6,634,358 B2 | 10/2003 | Kwok et al. |
| 6,637,434 B2 | 10/2003 | Noble |
| 6,644,315 B2 | 11/2003 | Ziaee |
| 6,644,316 B2 | 11/2003 | Bowman et al. |
| 6,651,658 B1 | 11/2003 | Hill et al. |
| 6,651,663 B2 | 11/2003 | Barnett et al. |
| 6,659,102 B1 | 12/2003 | Sico |
| 6,662,803 B2 | 12/2003 | Gradon et al. |
| 6,668,828 B1 | 12/2003 | Figley et al. |
| 6,679,257 B1 | 1/2004 | Robertson et al. |
| 6,679,265 B2 | 1/2004 | Strickland et al. |
| 6,691,707 B1 | 2/2004 | Gunaratnam et al. |
| 6,712,072 B1 | 3/2004 | Lang |
| 6,729,333 B2 | 5/2004 | Barnett et al. |
| 6,736,139 B1 | 5/2004 | Wix |
| 6,772,761 B1 | 8/2004 | Rucker, Jr. |
| 6,796,308 B2 | 9/2004 | Gunaratnam et al. |
| 6,851,425 B2 | 2/2005 | Jaffre et al. |
| 6,851,428 B2 | 2/2005 | Dennis |
| 6,883,177 B1 | 4/2005 | Ouellette et al. |
| 6,889,692 B2 | 5/2005 | Hollis |
| 6,892,729 B2 | 5/2005 | Smith et al. |
| 6,895,965 B2 | 5/2005 | Scarberry et al. |
| 6,907,882 B2 | 6/2005 | Ging et al. |
| 6,918,390 B2 | 7/2005 | Lithgow et al. |
| 6,951,218 B2 | 10/2005 | Gradon et al. |
| 6,953,354 B2 | 10/2005 | Edirisuriya et al. |
| 7,004,165 B1 | 2/2006 | Salcido |
| 7,007,696 B2 | 3/2006 | Palkon et al. |
| 7,021,311 B2 | 4/2006 | Gunaratnam et al. |
| 7,066,178 B2 | 6/2006 | Gunaratnam et al. |
| 7,066,179 B2 | 6/2006 | Eaton et al. |
| 7,077,126 B2 | 7/2006 | Kummer et al. |
| 7,089,939 B2 | 8/2006 | Walker et al. |
| 7,096,864 B1 | 8/2006 | Mayer et al. |
| 7,111,624 B2 | 9/2006 | Thudor et al. |
| 7,174,893 B2 | 2/2007 | Walker et al. |
| 7,185,652 B2 | 3/2007 | Gunaratnam et al. |
| 7,185,653 B2 | 3/2007 | Lee |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| D550,834 S | 9/2007 | Samaras |
| 7,290,546 B2 | 11/2007 | Sprinkle et al. |
| 7,318,437 B2 | 1/2008 | Gunaratnam et al. |
| 7,353,827 B2 | 4/2008 | Geist |
| 7,406,966 B2 | 8/2008 | Wondka et al. |
| D582,546 S | 12/2008 | Fujiura et al. |
| D586,906 S | 2/2009 | Stallard et al. |
| 7,487,772 B2 | 2/2009 | Ging et al. |
| 7,523,754 B2 | 4/2009 | Lithgow et al. |
| D595,841 S | 7/2009 | McAuley et al. |
| 7,568,482 B2 | 8/2009 | Jaffre et al. |
| 7,597,100 B2 | 10/2009 | Ging et al. |
| 7,621,274 B2 * | 11/2009 | Sprinkle ............ A61M 16/0638 |
| | | 128/206.28 |
| 7,647,926 B2 | 1/2010 | Gerder et al. |
| 7,665,464 B2 | 2/2010 | Kopacko et al. |
| 7,681,575 B2 | 3/2010 | Wixey et al. |
| 7,694,677 B2 | 4/2010 | Tang |
| 7,762,260 B2 * | 7/2010 | Ho ..................... A61M 16/0633 |
| | | 128/207.11 |
| 7,779,832 B1 | 8/2010 | Ho et al. |
| 7,814,911 B2 | 10/2010 | Bordewick et al. |
| 7,827,990 B1 | 11/2010 | Melidis et al. |
| 7,896,003 B2 | 3/2011 | Matula et al. |
| D635,661 S | 4/2011 | Stallard et al. |
| 7,931,024 B2 | 4/2011 | Ho et al. |
| 7,931,025 B2 | 4/2011 | Eaton et al. |
| D639,420 S | 6/2011 | D'Souza et al. |
| 8,025,057 B2 * | 9/2011 | Ging ................. A61M 16/0057 |
| | | 128/207.11 |
| 8,042,539 B2 | 10/2011 | Chandran et al. |
| 8,042,542 B2 | 10/2011 | Ging et al. |
| D652,914 S | 1/2012 | D'Souza et al. |
| 8,091,547 B2 | 1/2012 | Thudor et al. |
| 8,136,524 B2 | 3/2012 | Ging et al. |
| 8,186,345 B2 | 5/2012 | Payton et al. |
| 8,342,181 B2 | 1/2013 | Selvarajan et al. |
| 8,353,293 B1 | 1/2013 | Fuhrman |
| 8,371,302 B2 | 2/2013 | Ging et al. |
| D681,192 S | 4/2013 | D'Souza et al. |
| D683,447 S | 5/2013 | Olsen et al. |
| 8,434,485 B2 | 5/2013 | Osier |
| 8,443,807 B2 | 5/2013 | McAuley et al. |
| 8,453,641 B2 | 6/2013 | Payton et al. |

(56) References Cited

U.S. PATENT DOCUMENTS

| | | |
|---|---|---|
| 8,479,726 B2 | 7/2013 | McAuley |
| 8,479,741 B2 | 7/2013 | McAuley et al. |
| 8,517,023 B2 | 8/2013 | Henry |
| 8,517,024 B2 | 8/2013 | Selvarajan et al. |
| 8,550,072 B2 | 10/2013 | Thudor et al. |
| 8,550,084 B2 | 10/2013 | Ng et al. |
| 8,567,404 B2 | 10/2013 | Davidson et al. |
| D693,459 S | 11/2013 | Prentice et al. |
| D693,460 S | 11/2013 | Rothemel |
| D693,461 S | 11/2013 | Rothermel |
| D693,462 S | 11/2013 | Rothemmel |
| D695,887 S | 12/2013 | Ozolins |
| 8,596,274 B2 * | 12/2013 | Hieber .............. A61M 16/0644 128/201.23 |
| 8,596,276 B2 | 12/2013 | Omura et al. |
| D697,203 S | 1/2014 | Clarke |
| 8,631,793 B2 | 1/2014 | Omura et al. |
| 8,636,005 B2 | 1/2014 | Gradon et al. |
| 8,701,667 B1 | 4/2014 | Ho et al. |
| 8,714,157 B2 | 5/2014 | McAuley et al. |
| D706,413 S | 6/2014 | Veliss |
| D707,349 S | 6/2014 | D'Souza |
| 8,752,254 B2 | 6/2014 | Perner |
| 8,757,157 B2 | 6/2014 | Price et al. |
| 8,783,257 B2 | 7/2014 | McAuley et al. |
| D716,440 S | 10/2014 | D'Souza et al. |
| 8,944,061 B2 | 2/2015 | D'souza et al. |
| 8,950,404 B2 | 2/2015 | Formica et al. |
| 8,960,196 B2 | 2/2015 | Henry |
| 9,027,556 B2 | 5/2015 | Ng et al. |
| 9,032,955 B2 * | 5/2015 | Lubke .............. A61M 16/0683 128/206.21 |
| 9,032,995 B2 | 5/2015 | Spiegel |
| 9,072,852 B2 | 7/2015 | McAuley et al. |
| 9,119,929 B2 | 9/2015 | McAuley et al. |
| 9,119,931 B2 | 9/2015 | D'Souza et al. |
| 9,132,256 B2 | 9/2015 | Gunaratnam et al. |
| 9,138,555 B2 | 9/2015 | McAuley et al. |
| 9,144,655 B2 | 9/2015 | McAuley et al. |
| 9,149,596 B2 | 10/2015 | Valcic et al. |
| 9,242,062 B2 | 1/2016 | Melidis et al. |
| 9,265,902 B2 | 2/2016 | Payton et al. |
| D751,188 S | 3/2016 | Skipper |
| 9,272,109 B2 | 3/2016 | Rothermel et al. |
| 9,292,799 B2 | 3/2016 | McAuley et al. |
| D753,813 S | 4/2016 | Ozolins |
| 9,302,065 B2 | 4/2016 | Smith |
| 9,320,566 B1 | 4/2016 | Alston, Jr. et al. |
| 9,333,315 B2 | 5/2016 | McAuley et al. |
| 9,339,621 B2 | 5/2016 | McAuley et al. |
| 9,339,624 B2 | 5/2016 | McAuley et al. |
| 9,375,545 B2 | 6/2016 | Darkin et al. |
| 9,381,316 B2 | 7/2016 | Ng et al. |
| D764,049 S | 8/2016 | Cullen |
| D767,755 S | 9/2016 | D'Souza |
| D769,440 S | 10/2016 | Amarasinghe |
| 9,517,319 B2 | 12/2016 | Omura |
| 9,522,246 B2 | 12/2016 | Frater et al. |
| D782,030 S | 3/2017 | Prentice et al. |
| D782,031 S | 3/2017 | Prentice et al. |
| D784,515 S | 4/2017 | Prentice |
| D784,516 S | 4/2017 | Prentice et al. |
| D797,277 S | 9/2017 | Blanch |
| D809,132 S | 1/2018 | Bornholdt |
| D809,649 S | 2/2018 | Bornholdt |
| D810,277 S | 2/2018 | Amarasinghe |
| D814,020 S | 3/2018 | Bornholdt |
| D821,569 S | 6/2018 | Bornholdt |
| D824,021 S | 7/2018 | Prentice |
| D824,511 S | 7/2018 | Prentice |
| D837,972 S | 1/2019 | Bornholdt |
| D838,838 S | 1/2019 | Bowsher |
| 10,413,692 B2 | 9/2019 | Law |
| D870,266 S | 12/2019 | Bornholdt |
| D882,066 S | 4/2020 | Niccol et al. |
| D892,307 S | 8/2020 | Wang |
| 11,027,087 B2 | 6/2021 | Olsen et al. |
| 11,173,270 B2 | 11/2021 | Bornholdt et al. |
| 11,179,537 B2 | 11/2021 | Bornholdt et al. |
| 11,638,800 B2 | 5/2023 | McLaren |
| 11,819,612 B2 | 11/2023 | Nelson |
| D1,010,103 S | 1/2024 | Niccol et al. |
| 2001/0017134 A1 | 8/2001 | Bahr |
| 2001/0020474 A1 | 9/2001 | Hecker et al. |
| 2002/0014241 A1 | 2/2002 | Gradon et al. |
| 2002/0020416 A1 | 2/2002 | Namey |
| 2002/0026934 A1 | 3/2002 | Lithgow et al. |
| 2002/0029780 A1 | 3/2002 | Frater |
| 2002/0040515 A1 | 4/2002 | Uehara et al. |
| 2002/0053347 A1 | 5/2002 | Ziaee |
| 2002/0100479 A1 | 8/2002 | Scarberry et al. |
| 2003/0019495 A1 | 1/2003 | Palkon et al. |
| 2003/0019496 A1 | 1/2003 | Kopacko et al. |
| 2003/0029454 A1 | 2/2003 | Gelinas et al. |
| 2003/0037788 A1 | 2/2003 | Gallem et al. |
| 2003/0051732 A1 | 3/2003 | Smith et al. |
| 2003/0075180 A1 | 4/2003 | Raje et al. |
| 2003/0089373 A1 | 5/2003 | Gradon et al. |
| 2003/0127101 A1 | 7/2003 | Carnell |
| 2003/0149384 A1 | 8/2003 | Davis et al. |
| 2003/0196655 A1 | 10/2003 | Ging et al. |
| 2003/0196658 A1 | 10/2003 | Ging et al. |
| 2003/0217746 A1 | 11/2003 | Gradon et al. |
| 2003/0236015 A1 | 12/2003 | Edirisuriya et al. |
| 2004/0025882 A1 | 2/2004 | Madaus et al. |
| 2004/0035427 A1 | 2/2004 | Bordewick et al. |
| 2004/0065328 A1 | 4/2004 | Amarasinghe et al. |
| 2004/0067333 A1 | 4/2004 | Amarasinghe |
| 2004/0094157 A1 | 5/2004 | Dantanarayana et al. |
| 2004/0118406 A1 | 6/2004 | Lithgow et al. |
| 2004/0118412 A1 | 6/2004 | Piletti-Reyes |
| 2004/0134497 A1 | 7/2004 | Gunaratnam et al. |
| 2004/0149280 A1 | 8/2004 | Semeniuk |
| 2004/0182398 A1 | 9/2004 | Sprinkle et al. |
| 2004/0226566 A1 | 11/2004 | Gunaratnam et al. |
| 2005/0011524 A1 | 1/2005 | Thomlinson et al. |
| 2005/0155603 A1 | 7/2005 | Frerichs et al. |
| 2005/0155604 A1 | 7/2005 | Ging et al. |
| 2005/0199239 A1 | 9/2005 | Lang et al. |
| 2006/0042629 A1 | 3/2006 | Geist |
| 2006/0060200 A1 | 3/2006 | Ho et al. |
| 2006/0076019 A1 | 4/2006 | Ho et al. |
| 2006/0096598 A1 | 5/2006 | Ho et al. |
| 2006/0124131 A1 | 6/2006 | Chandran et al. |
| 2006/0130844 A1 | 6/2006 | Ho et al. |
| 2006/0169286 A1 | 8/2006 | Eifler et al. |
| 2006/0196511 A1 | 9/2006 | Lau et al. |
| 2006/0201514 A1 | 9/2006 | Jones et al. |
| 2006/0207599 A1 | 9/2006 | Busch et al. |
| 2006/0254593 A1 | 11/2006 | Chang |
| 2006/0283459 A1 | 12/2006 | Geiselhart et al. |
| 2007/0044804 A1 | 3/2007 | Matula, Jr. et al. |
| 2007/0125385 A1 | 6/2007 | Ho et al. |
| 2007/0163600 A1 | 7/2007 | Hoffman |
| 2007/0209663 A1 | 9/2007 | Marque et al. |
| 2007/0215161 A1 | 9/2007 | Frater et al. |
| 2007/0221227 A1 | 9/2007 | Ho |
| 2007/0250109 A1 | 10/2007 | Kerstein et al. |
| 2007/0267017 A1 | 11/2007 | McAuley et al. |
| 2008/0035152 A1 | 2/2008 | Ho et al. |
| 2008/0110464 A1 | 5/2008 | Davidson et al. |
| 2008/0178875 A1 | 7/2008 | Henry |
| 2008/0223373 A1 | 9/2008 | Chang |
| 2008/0257354 A1 | 10/2008 | Davidson et al. |
| 2008/0302366 A1 | 12/2008 | McGinnis et al. |
| 2009/0014008 A1 | 1/2009 | Takishita et al. |
| 2009/0032024 A1 | 2/2009 | Burz et al. |
| 2009/0038619 A1 | 2/2009 | Ho et al. |
| 2009/0044808 A1 | 2/2009 | Guney et al. |
| 2009/0050156 A1 | 2/2009 | Ng et al. |
| 2009/0065729 A1 | 3/2009 | Worboys et al. |
| 2009/0095301 A1 | 4/2009 | Hitchcock et al. |
| 2009/0114227 A1 | 5/2009 | Gunaratnam et al. |
| 2009/0126739 A1 | 5/2009 | Ng et al. |

(56) References Cited

U.S. PATENT DOCUMENTS

| | | |
|---|---|---|
| 2009/0139526 A1 | 6/2009 | Melidis et al. |
| 2009/0139527 A1 | 6/2009 | Ng et al. |
| 2009/0178679 A1 | 7/2009 | Lithgow et al. |
| 2009/0188505 A1 | 7/2009 | Smart et al. |
| 2009/0223519 A1 | 9/2009 | Eifler et al. |
| 2009/0272380 A1 | 11/2009 | Jaffre et al. |
| 2010/0006101 A1 | 1/2010 | McAuley et al. |
| 2010/0108072 A1 | 5/2010 | D'Souza et al. |
| 2010/0229868 A1 | 9/2010 | Rummery et al. |
| 2010/0282265 A1 | 11/2010 | Melidis et al. |
| 2010/0307502 A1 | 12/2010 | Rummery et al. |
| 2010/0319700 A1 | 12/2010 | Ng et al. |
| 2011/0005524 A1 | 1/2011 | Veliss et al. |
| 2011/0048425 A1 | 3/2011 | Chang |
| 2011/0072553 A1 | 3/2011 | Ho et al. |
| 2011/0146685 A1 | 6/2011 | Allan |
| 2011/0259335 A1* | 10/2011 | Sullivan ............... A62B 18/084 128/207.18 |
| 2011/0308526 A1 | 12/2011 | Ho et al. |
| 2012/0103340 A1 | 5/2012 | Chu et al. |
| 2012/0138060 A1 | 6/2012 | Barlow |
| 2012/0138061 A1 | 6/2012 | Dravitzki et al. |
| 2012/0175488 A1 | 7/2012 | Xu |
| 2012/0190998 A1 | 7/2012 | Armitstead et al. |
| 2012/0199132 A1 | 8/2012 | Ho et al. |
| 2012/0216819 A1 | 8/2012 | Raje et al. |
| 2012/0222680 A1 | 9/2012 | Eves et al. |
| 2012/0234326 A1 | 9/2012 | Mazzone et al. |
| 2012/0285452 A1 | 11/2012 | Amirav et al. |
| 2013/0008449 A1 | 1/2013 | Busch et al. |
| 2013/0092169 A1 | 4/2013 | Frater et al. |
| 2013/0186404 A1 | 7/2013 | Chien |
| 2013/0199537 A1* | 8/2013 | Formica ............ A61M 16/0875 128/205.25 |
| 2013/0220327 A1 | 8/2013 | Barlow et al. |
| 2013/0228173 A1 | 9/2013 | Busch |
| 2013/0306066 A1 | 11/2013 | Selvarajan et al. |
| 2013/0319419 A1 | 12/2013 | Lee |
| 2014/0096774 A1 | 4/2014 | Olen et al. |
| 2014/0166018 A1 | 6/2014 | Dravitzki et al. |
| 2014/0174446 A1 | 6/2014 | Prentice et al. |
| 2014/0224255 A1 | 8/2014 | McCaslin et al. |
| 2014/0283842 A1 | 9/2014 | Bearne et al. |
| 2014/0305433 A1 | 10/2014 | Rothermel |
| 2014/0311494 A1 | 10/2014 | Gibson et al. |
| 2015/0090266 A1 | 4/2015 | Melidis et al. |
| 2015/0352306 A1 | 12/2015 | Scheiner et al. |
| 2016/0001028 A1 | 1/2016 | McAuley et al. |
| 2016/0008558 A1 | 1/2016 | Huddart et al. |
| 2016/0045700 A1 | 2/2016 | Amarasinghe |
| 2016/0051786 A1 | 2/2016 | McAuley et al. |
| 2016/0067442 A1 | 3/2016 | Salmon et al. |
| 2016/0213873 A1 | 7/2016 | McAuley et al. |
| 2016/0213874 A1 | 7/2016 | Davidson et al. |
| 2016/0220781 A1 | 8/2016 | Arrowsmith et al. |
| 2016/0310687 A1 | 10/2016 | McAuley et al. |
| 2016/0325067 A1 | 11/2016 | Harwood |
| 2016/0354572 A1 | 12/2016 | Lim et al. |
| 2017/0028148 A1 | 2/2017 | McAuley et al. |
| 2017/0065786 A1 | 3/2017 | Stephenson et al. |
| 2017/0157353 A1 | 6/2017 | Olsen |
| 2018/0008794 A1 | 1/2018 | Salmon |
| 2018/0185598 A1 | 7/2018 | Olsen |
| 2018/0361095 A1 | 12/2018 | Frerichs |
| 2020/0108989 A1 | 4/2020 | Hammer |
| 2021/0187234 A1 | 6/2021 | Tebbutt |
| 2022/0031991 A1 | 2/2022 | Bornholdt et al. |

FOREIGN PATENT DOCUMENTS

| | | |
|---|---|---|
| AU | 2003257274 | 3/2004 |
| AU | 2008906390 | 12/2008 |
| AU | 2009900327 | 1/2009 |
| AU | 2009902731 | 6/2009 |
| AU | 2009904236 | 9/2009 |
| AU | 2014202233 A1 | 5/2014 |
| CA | 1311662 | 12/1992 |
| CN | 2060293 | 8/1990 |
| CN | 2172538 | 7/1994 |
| CN | 1784250 | 6/2006 |
| CN | 101450239 | 6/2009 |
| CN | 201275352 | 7/2009 |
| CN | 101951984 | 1/2011 |
| CN | 202842549 | 4/2013 |
| DE | 895692 | 11/1953 |
| DE | 3026375 | 2/1982 |
| DE | 19603949 | 8/1997 |
| DE | 19962515 | 7/2001 |
| DE | 20062009768 U | 8/2006 |
| DE | 202006009768 | 8/2006 |
| DE | 102006011151 | 9/2007 |
| DE | 20 2014 104150 | 9/2014 |
| EP | 0 427 474 | 11/1990 |
| EP | 0 303 090 | 4/1992 |
| EP | 0 747 078 | 12/1996 |
| EP | 0 982 042 | 3/2000 |
| EP | 1 099 452 | 5/2001 |
| EP | 1 245 250 | 10/2002 |
| EP | 1 258 266 | 11/2002 |
| EP | 1606023 | 12/2005 |
| EP | 2 130 563 | 12/2009 |
| EP | 2 417 994 | 2/2012 |
| EP | 2281596 | 10/2012 |
| EP | 2 668 971 | 12/2012 |
| EP | 2818194 | 12/2014 |
| EP | 2 954 920 | 12/2015 |
| EP | 3693047 | 8/2020 |
| FR | 1299470 | 6/1962 |
| FR | 2658725 | 8/1991 |
| FR | 2749176 | 12/1997 |
| GB | 190224431 | 12/1902 |
| GB | 309770 | 4/1929 |
| GB | 823897 | 11/1959 |
| GB | 880824 | 10/1961 |
| GB | 979357 | 1/1965 |
| GB | 1467828 | 3/1977 |
| GB | 2133275 | 7/1984 |
| GB | 2173274 | 10/1986 |
| GB | 2343722 | 5/2002 |
| GB | 2393126 | 11/2004 |
| GB | 2385533 | 8/2005 |
| GB | 2426711 | 12/2006 |
| JP | H09-010311 | 1/1997 |
| JP | 11-000397 | 1/1999 |
| JP | 2000-325481 | 11/2000 |
| JP | 2004-016488 | 1/2004 |
| JP | 2005-529687 | 10/2005 |
| JP | 2007-516750 | 6/2007 |
| JP | 2007-527271 | 9/2007 |
| JP | 2008-526393 | 7/2008 |
| KR | 20130000253 | 1/2013 |
| NZ | 573196 | 7/2010 |
| NZ | 556198 | 10/2010 |
| NZ | 556043 | 1/2011 |
| NZ | 551715 | 2/2011 |
| RU | 2186597 | 8/2002 |
| SU | 726692 | 9/1981 |
| WO | WO 82/003548 | 10/1982 |
| WO | WO 98/04310 | 2/1998 |
| WO | WO 98/04311 | 2/1998 |
| WO | WO 98/18514 | 5/1998 |
| WO | WO 98/024499 | 6/1998 |
| WO | WO 98/048878 | 11/1998 |
| WO | WO 98/57691 | 12/1998 |
| WO | WO 99/04842 | 2/1999 |
| WO | WO 99/021618 | 5/1999 |
| WO | WO 99/58181 | 11/1999 |
| WO | WO 99/058198 | 11/1999 |
| WO | WO 00/50122 | 8/2000 |
| WO | WO 00/057942 | 10/2000 |
| WO | WO 00/069497 | 11/2000 |
| WO | WO 00/074758 | 12/2000 |
| WO | WO 00/78381 | 12/2000 |

(56) References Cited

FOREIGN PATENT DOCUMENTS

| | | |
|---|---|---|
| WO | WO 00/078384 | 12/2000 |
| WO | WO 01/000266 | 1/2001 |
| WO | WO 01/041854 | 6/2001 |
| WO | WO 01/062326 | 8/2001 |
| WO | WO 01/97892 | 12/2001 |
| WO | WO 01/097893 | 12/2001 |
| WO | WO 02/011804 | 2/2002 |
| WO | WO 02/047749 | 6/2002 |
| WO | WO 02/074372 | 9/2002 |
| WO | WO 03/090827 | 11/2003 |
| WO | WO 03/092755 | 11/2003 |
| WO | WO 04/007010 | 1/2004 |
| WO | WO 04/021960 | 3/2004 |
| WO | WO 04/022146 | 3/2004 |
| WO | WO 04/022147 | 3/2004 |
| WO | WO 04/030736 | 4/2004 |
| WO | WO 04/041341 | 5/2004 |
| WO | WO 04/041342 | 5/2004 |
| WO | WO 04/071565 | 8/2004 |
| WO | WO 04/073778 | 9/2004 |
| WO | WO 05/009521 | 2/2005 |
| WO | WO 05/018523 | 3/2005 |
| WO | WO 05/021075 | 3/2005 |
| WO | WO 05/051468 | 6/2005 |
| WO | WO 05/063328 | 7/2005 |
| WO | WO 05/068002 | 7/2005 |
| WO | WO 05/079726 | 9/2005 |
| WO | WO 05/086946 | 9/2005 |
| WO | WO 05/097247 | 10/2005 |
| WO | WO 05/123166 | 12/2005 |
| WO | WO 06/000046 | 1/2006 |
| WO | WO 06/069415 | 7/2006 |
| WO | WO 06/074513 | 7/2006 |
| WO | WO 06/074514 | 7/2006 |
| WO | WO 06/074515 | 7/2006 |
| WO | WO 06/096924 | 9/2006 |
| WO | WO 06/130903 | 12/2006 |
| WO | WO 06/138416 | 12/2006 |
| WO | WO 07/009182 | 1/2007 |
| WO | WO 07/022562 | 3/2007 |
| WO | WO 07/041751 | 4/2007 |
| WO | WO 07/041786 | 4/2007 |
| WO | WO 07/045008 | 4/2007 |
| WO | WO 07/048174 | 5/2007 |
| WO | WO 07/050557 | 5/2007 |
| WO | WO 07/139531 | 12/2007 |
| WO | WO 07/147088 | 12/2007 |
| WO | WO 08/007985 | 1/2008 |
| WO | WO 08/030831 | 3/2008 |
| WO | WO 08/040050 | 4/2008 |
| WO | WO 08/060295 | 5/2008 |
| WO | WO 08/070929 | 6/2008 |
| WO | WO 08/106716 | 9/2008 |
| WO | WO 08/148086 | 12/2008 |
| WO | WO 09/002608 | 12/2008 |
| WO | WO 09/026627 | 3/2009 |
| WO | WO 09/052560 | 4/2009 |
| WO | WO 2009/059353 | 5/2009 |
| WO | WO 09/092057 | 7/2009 |
| WO | WO 09/108995 | 9/2009 |
| WO | WO 09/139647 | 11/2009 |
| WO | WO 10/009877 | 1/2010 |
| WO | WO 10/066004 | 6/2010 |
| WO | WO 10/067237 | 6/2010 |
| WO | WO 10/071453 | 6/2010 |
| WO | WO 10/073142 | 7/2010 |
| WO | WO 10/131189 | 11/2010 |
| WO | WO 10/135785 | 12/2010 |
| WO | WO 11/014931 | 2/2011 |
| WO | WO 11/060479 | 5/2011 |
| WO | WO 11/077254 | 6/2011 |
| WO | WO 11/078703 | 6/2011 |
| WO | WO 12/020359 | 2/2012 |
| WO | WO 12/040791 | 4/2012 |
| WO | WO 12/045127 | 4/2012 |
| WO | WO 12/140514 | 10/2012 |
| WO | WO 13/006899 | 1/2013 |
| WO | WO 13/064950 | 5/2013 |
| WO | WO 13/066195 | 5/2013 |
| WO | WO 2013/061260 | 5/2013 |
| WO | WO 2013/168041 | 11/2013 |
| WO | WO 14/020469 | 2/2014 |
| WO | WO 2014/020481 | 2/2014 |
| WO | WO 14/062070 | 4/2014 |
| WO | WO 14/129913 | 8/2014 |
| WO | WO 14/174393 | 10/2014 |
| WO | WO 14/175753 | 10/2014 |
| WO | WO 15/022629 | 2/2015 |
| WO | WO 15/033287 | 3/2015 |
| WO | WO 15/057087 | 4/2015 |
| WO | WO 15/079396 | 6/2015 |
| WO | WO 2016/009393 | 1/2016 |
| WO | WO 16/032343 | 3/2016 |
| WO | WO 16/033857 | 3/2016 |
| WO | WO 16/139623 | 9/2016 |
| WO | WO 17/049356 | 3/2017 |
| WO | WO 17/049357 | 3/2017 |

OTHER PUBLICATIONS

U.S. Appl. No. 61/064,406, filed Mar. 4, 2008, Wehbeh.
U.S. Appl. No. 61/071,893, filed May 23, 2008, Wehbeh et al.
U.S. Appl. No. 61/136,617, filed Feb. 23, 2009, Wehbeh et al.
American Heritage Dictionary of the English Language, Fourth Edition (2006), pp. 3-5.
Answer of ResMed Corp. to Complaint for Patent Infringement and Counterclaims, *Fisher & Paykel Healthcare Ltd.* v. *ResMed Corp.*, Case No. 3:16-cv-02068-DMS-WVG (S.D. Cal.), filed Oct. 27, 2016, 9 pages.
Complaint for Patent Infringement, *ResMed Inc.* v. *Fisher & Paykel Healthcare Corp. Ltd.*, Case No. 3:16-cv-02072-JLS-MDD (S.D. Cal.) Aug. 16, 2016.
Complaint of ResMed Ltd, ResMed Inc., and ResMed Corp. Under Section 337 of the Tariff Act of 1930, as amended, Investigation No. 337-TA-1022, Aug. 17, 2016.
File History of U.S. Pat. No. 8,944,061, filed Mar. 15, 2013, Excerpts, 437 pages.
File History of U.S. Pat. No. 8,950,404, filed Apr. 19, 2011, Excerpts, 666 pages.
File History of U.S. Pat. No. 8,960,196, filed May 29, 2013 Excerpts, 51 pages.
File History of U.S. Pat. No. 9,119,931, Excerpts, 731 pages.
File History of U.S. Pat. No. 9,381,316, filed Jan. 30, 2009 Excerpts, 655 pages.
File History of U.S. Pat. No. 9,522,246 filed Feb. 6, 2015, Excerpts, 261 pages.
Fisher & Paykel FlexFit 431 Full Face Mask Specification Sheet.
Fisher & Paykel HC200 Series Nasal CPAP Blower & Heated Humidifier User Manual by Fischer & Paykel Healthcare, May 1998, 17 Pages.
Fisher & Paykel Healthcare Limited, Simplus Full Face Mask, 185048005 REVA, 2012.
Fisher & Paykel MR810 Respiratory Humidifier Technical Manual, Revision C, 2004, Fischer & Paykel Healthcare Ltd, Auckland New Zealand, 43 pages.
Introducing the F&P Nivairo RT045 Full Face NIV Mask by F&P Healthcare. Youtube. Posting Date: Sep. 19, 2017. Retrieval date: Feb. 8, 2022. Retrieved from internet: https://www.youtube.com/watch?v=N9fOSb-y0eQ (Year: 2017).
Malloy, 1994, Plastic Part Design for Injection Molding, Hanswer Gardner Publications, Inc, Cincinnati, OH, 14 pp.
Merriam-Webster's Collegiate Dictionary, Eleventh Edition, 2004, pp. 703, 905, 1074, 1184.
Oxford American College Dictionary Excerpts, p. 7, 2002.
Patent Owner's Complaint for *Fisher & Paykel Healthcare Ltd.* v. *ResMed Corp.*, Case No. 2:16-cv-06099-R-AJW (C.D. Cal.), filed Aug. 15, 2016, 29 pages.

(56) References Cited

OTHER PUBLICATIONS

Patent Owner's Complaint for *Fisher & Paykel Healthcare Ltd.* v. *ResMed Corp.*, Case No. 3:16-cv-02068-GPC-WVG (S.D. Cal.) filed Aug. 16, 2016, 29 pages.
Petition for Inter Partes Review of U.S. Pat. No. 8,443,807 Pursuant to 35 U.S.C. §§ 311-19, 37 C.F.R. § 42, IPR2016-01726, filed Sep. 7, 2016, 74 pages.
Petition for Inter Partes Review of U.S. Pat. No. 8,443,807 Pursuant to 35 U.S.C. §§ 311-19, 37 C.F.R. § 42, IPR2016-01734, filed Sep. 7, 2016, 74 pages.
Petition for Inter Partes Review of U.S. Pat. No. 8,479,741 Pursuant to 35 U.S.C. §§ 311-19, 37 C.F.R. § 42, IPR2016-01714, filed Sep. 7, 2016, 61 pages.
Petition for Inter Partes Review of U.S. Pat. No. 8,479,741 Pursuant to 35 U.S.C. §§ 311-19, 37 C.F.R. § 42, IPR2016-01718, filed Sep. 7, 2016, 65 pages.
Petitioners' Complaint for *ResMed Inc., et al.* v. *Fisher & Paykel Healthcare Corp. Ltd., et al.*, Case No. 3:16-cv-02072-JAH-MDD (S.D. Cal.), filed Aug. 16, 2016, 65 pages.
Philips Respironics "System One Heated Humidifier-User Manual", 2011, pp. 1-16, [retrivied on Nov. 25, 2013] from the internet: URL: http://www.cpapxchange.com/cpap-machines-biap-machines/system-one-60-series-cpap-humidifier-manual.pdf front cover, pp. 3-4 and 6.
ResMed Origins Brochure (Retrieved Apr. 17, 2016 from http://www.resmed.com/us/dam/documents/articles/resmedorigins.pdf).
ResMed Ultra Mirage brochure, 2004.
ResMed Webpage from Jun. 29, 1997 (Source: Wayback Machine Internet Archive); http://web.archive.org/web/19970629053430/http://www.resmed.com/maskframes/mask.htm.
ResMed, Mirage Swift™ Nasal Pillows System from ResMed, product brochure, 2004, 6 pp.
ResMed, Mirage Swift™ Nasal Pillows System: User's Guide, product brochure, 2004, 11 pp.
ResMed, Mirage Vista™ Nasal Mask: Components Card, product brochure, 2005, 1 p.
Statutory Declaration made by Alistair Edwin McAuley, Apr. 9, 2015, in the matter of an Opposition by Fisher & Paykel Healthcare Limited of Australian patent application 2009221630 in the name of ResMed Limited.
Webster's II New College Dictionary Excerpts, 3rd ed., 2005, p. 7.
International Search Report, PCT/IB2015/055412, dated Oct. 12, 2015 in 6 pages.

* cited by examiner

HEADGEAR CLIP ARRANGEMENT

INCORPORATION BY REFERENCE TO ANY PRIORITY APPLICATIONS

Any and all applications to which priority is claimed are hereby incorporated by reference herein and made a part of the present disclosure.

BACKGROUND

Technical Field

The present disclosure generally relates to masks for use in providing respiratory therapies such as, but not limited to, constant positive airway pressure (CPAP) and non-invasive ventilation (NIV). More particularly, the present disclosure relates to a headgear connection assembly configured to provide improved reliability and ease of use for full face, nasal, nasal pillows, cannulas, and other masks or interfaces.

Description of Related Art

Respiratory masks are used to provide therapies for the treatment of a variety of respiratory conditions including but not limited to CPAP and NIV. The present disclosure will be described in relation to CPAP therapy, however it is to be understood that it may be equally applicable to other therapies.

CPAP therapy is used in the treatment of obstructive sleep apnea (OSA), a condition in which the back of the throat relaxes so much while sleeping that it narrows or entirely blocks the airway. With the constriction or closure of the airway, breathing can stop or become very shallow for a few seconds or longer. CPAP splints open the airway by providing a constant flow of pressurized air to the airway via an interface such as a mask. For the therapy to be effective, a substantially leak free seal ideally should be maintained between the mask and a user's face. In order to achieve this, a headgear system can be used to secure the mask to a user's face. It is commonly known in the art for there to be a headgear connection assembly between a headgear and a mask. The headgear connection may include a fastening means, such as but not limited to, hooks, loops and clips that allow the headgear to be selectively attached and detached.

Some characteristics that exist with prior headgear connection assemblies include fasteners being difficult to attach to and/or detach from the mask, fasteners detaching undesirably during use, resulting in leaks and/or loss of therapy, or fasteners providing too much or too little mobility in the connection between headgear and mask, which may impact the ease with which a mask is fitted and/or user comfort. These characteristics may lead to the mask and headgear system lacking a desirable level of ease of use, reliability and/or comfort, which in turn may result in less-than-ideal user compliance.

It is an objective of one or more embodiments disclosed herein to at least partially address one or more of these characteristics. Alternatively, it is an object to at least provide a useful choice to the public.

BRIEF SUMMARY

According to a first aspect of the presently disclosed subject matter, there is provided a headgear connection assembly for a respiratory mask, the headgear connection including a clip and a clip attachment portion. The clip attachment portion includes a post and a clip receiving opening. The clip includes a hook configured to engage with the post, a headgear attachment loop, and one or more finger grips. The hook includes a central portion, two outer portions and an interference bump.

According to a second aspect of the presently disclosed subject matter, the clip attachment portion further comprises a stop bump configured to restrict unwanted rotation of the clip when assembled.

Further aspects of the presently disclosed subject matter, which should be considered in all its novel aspects, will become apparent to those skilled in the art upon reading of the following description which provides at least one example of a practical application of the invention.

In some configurations, a clip connector for connecting a headgear to a mask body includes a body portion configured for attachment to the headgear. A hook portion defines a U-shape having a first leg, a second leg and an entrance to a space between the first leg and the second leg. The hook portion can comprise a central portion, a pair of outer portions positioned on opposing sides of the central portion. Each of the central portion and the pair of outer portions define a portion of both the first leg and the second leg. An interference bump can be provided on at least one of the central portion and the pair of outer portions. The interference bump extends into the entrance to the space. The central portion and the pair of outer portions are configured to flex independently of one another.

In some configurations, a width of the entrance at the interference bump is smaller than a width of an attachment structure of the mask body configured to be received within the space of the hook portion.

In some configurations, only the central portion includes the interference bump and flexes to allow an attachment structure of the mask body to be introduced into the space of the hook portion.

In some configurations, only the outer portions include the interference bumps and flex to allow an attachment structure of the mask body to be introduced into the space of the hook portion.

In some configurations, at least the ones of the central portion and outer portions without the interference bump accommodates a tension force of the headgear in use.

In some configurations, a slot is provided between the central portion and each of the outer portions.

In some configurations, the slot extends through first leg and second leg of the hook portion.

In some configurations, the slots are filled with an elastic filler material.

In some configurations, the filler material is overmolded onto the clip connector.

In some configurations, at least one finger grip portion is disposed on the body portion. The finger grip portion can be formed from a soft or elastic material.

In some configurations, the soft or elastic material of the finger grip portion is overmolded onto the body portion.

In some configurations, the at least one finger grip portion comprises first and second finger grip portions on opposing edges of the body portion of the clip connector.

In some configurations, the central portion is more flexible than the outer portions.

In some configurations, a mask assembly includes a mask body comprising a post and an opening adjacent the post and a clip connector, such as any of the clip connectors described in the preceding paragraphs. The post can be configured to be received within the space of the hook portion of the clip connector. The mask body can comprise a limitation bump within the opening that contacts the clip connector to limit rotation of the clip connector relative to the mask body.

In some configurations, the limitation bump limits one or both of rotation about an axis of the post and rotation normal to the axis of the post.

In some configurations, the limitation bump is located on an upper edge of the opening.

In some configurations, a respiratory mask is configured to deliver pressurized gas to a user. The mask is configured to attach to headgear by a connector clip having a body portion and a hook portion. The respiratory mask comprises a post configured to be received within a space of the hook portion of the connector clip. An opening is adjacent the post. A limitation bump is associated with the opening and is configured in use to contact the connector clip to limit rotation of the connector clip relative to the mask.

In some configurations, the limitation bump is located on an upper side of the opening and in use limits upward rotation of the connector clip, but permits downward rotation and disconnection of the connector clip from the post.

In some configurations, a width of the opening is configured to be equal to or smaller than a width of the body portion.

In some configurations, the limitation bump is configured to contact the body portion of the clip to limit rotation.

In some configurations, the limitation bump limits forward rotation of the connector clip.

In some configurations, rotation is limited to no more than 90 degrees.

In some configurations, a respiratory mask assembly includes a headgear, a connector clip having a body portion and a hook portion, and a respiratory mask, such as any of the respiratory masks described in the preceding paragraphs. The connector clip is configured to connect the headgear to the mask. The body portion is connected to the headgear. The hook portion is narrower than the body portion.

In some configurations, a connector arrangement comprising a connector clip for connecting a headgear to a mask body includes an attachment portion disposed on one of the mask body and the connector clip. A deflectable hook is disposed on the other of the mask body and the connector clip. A width of an entrance of the deflectable hook is narrower than a width of the attachment portion. The attachment portion is inserted through the entrance of the deflectable hook to connect the headgear to the mask body. An interference bump is disposed on the deflectable hook and protrudes in a direction that narrows the entrance of the deflectable hook. The interference bump inhibits the attachment portion from exiting through the entrance.

The deflectable hook can be selectively attached over the attachment portion via an interference fit between the attachment portion and the deflectable hook to connect the headgear to the mask body.

The interference bump can extend along the entire width of the deflectable hook.

The deflectable hook can include a center hook portion positioned between, adjacent to, and in alignment with outer hook portions. The center hook portion can be flexible independent of the outer hook portions.

An interference bump can be disposed on the center hook portion and protrude in a direction that narrows the entrance into the deflectable hook. The interference bump can prevent the attachment portion from exiting through the entrance.

An interference bump can be disposed on each of the center hook portion and the outer hook portions and protrude in a direction that narrows the entrance into the deflectable hook. Each interference bump can inhibit the attachment portion from exiting through the entrance.

Slots can separate the center hook portion and the outer hook portions.

The slots can be filled with elastic material.

The deflectable hook can further comprise elastic material over-molded onto outer surfaces of the deflectable hook.

The attachment portion can further comprise a cylindrical column, wherein the deflectable hook attaches over the cylindrical column.

The center hook portion can be more flexible than the outer hook portions.

In some configurations, a connection system for connecting a headgear to a mask body includes an attachment portion disposed on the mask body. The attachment portion can further comprise an opening disposed on the mask body, and a post disposed along an outer extent of the opening. A connector is disposed on the headgear. The connector can further comprise a body portion and a deflectable hook portion. The deflectable hook portion of the connector can be selectively attached over the post to connect the headgear to the mask body. The attachment portion can further comprise at least one stop bump positioned adjacent to the post along an extent of the opening. The stop bump can protrude a distance into the opening. The at least one stop bump can contacts the connector and block rotation of the connector to prevent the connector from rotating and detaching from the post.

A width of the body portion along a direction parallel to an axis of the post when the deflectable hook portion is connected to the post can be greater than a width of the opening along the direction parallel to the axis of the post.

A width of the body portion along a direction parallel to an axis of the post when the deflectable hook portion is connected to the post can be greater than a width of the deflectable hook portion along the direction parallel to the axis of the post when the deflectable hook portion is connected to the post.

The body portion can contact the mask body to limit a range of rotation of the connector about the post.

The range of rotation of the connector about the post can be 90 degrees or less.

The at least one stop bump can be positioned along an upper extent of the opening.

The at least one stop bump can extend a distance into the opening that is greater than the difference between the width of the opening along the direction parallel to an axis of the post and the width of the body portion along a direction parallel to the axis of the post when the deflectable hook portion is connected to the post.

The body portion can contact the at least one stop bump to limit a range of rotation of the connector about the post.

The range of rotation of the connector about the post can be 90 degrees or less.

An interference bump can be disposed on the deflectable hook portion and protrude in a direction towards a lower surface of the body portion. A distance between the interference bump and the lower surface of the body portion can be less than a width of the post.

The interference bump can extend along the entire width of the deflectable hook portion.

The deflectable hook portion can include a center hook portion positioned between, adjacent to, and in alignment with outer hook portions. The center hook portion can be flexible independent from the outer hook portions.

An interference bump can be disposed on the center hook portion and protrude in a direction towards a lower surface of the body portion. A distance between the interference bump and the lower surface of the body portion can be less than a width of the post.

An interference bump can be disposed on each of the center hook portion and the outer hook portions and protrude in a direction towards a lower surface of the body portion. A distance between each interference bump and the lower surface of the body portion can be less than a width of the post.

Slots can separate the center hook and the outer hooks.

The slots are filled with elastic material.

Finger grip portions can be disposed on the body portion. The finger grip portions can be formed from an elastic material.

The post can have a cylindrical cross-sectional shape.

The post can have a vertical orientation relative to the orientation of the mask body in use.

A protrusion can be disposed on the body portion and extend away from an outer surface of the body portion. The protrusion can contact the mask and limit rotation of the connector about the post to less than 90 degrees.

The deflectable hook portion can be narrower than the body portion.

Elastic material can be over-molded onto outer surfaces of the deflectable hook portion.

In some configurations, a method for attaching a headgear to a mask body, in which the mask body has an attachment portion including an opening disposed on the mask body and a post disposed along an outer extent of the opening, the headgear having a connector including a body portion and a hook portion connected to the body portion, and the hook portion having an entrance that is narrower than a width of the post, the method comprising aligning an entrance of the hook portion with the post, inserting the post through the entrance of the hook portion, the hook portion deflecting in a direction away from the post as the post travels through the entrance of the hook portion, selectively securing the hook portion onto the post to connect the headgear and the mask body, the hook portion deflecting to an undeflected shape after the post has traveled through the entrance of the hook portion, the entrance narrowing to block the post from exiting through the entrance, and limiting rotation of the connector about the post via at least one stop bump positioned adjacent to the post along an extent of the opening, the stop bump contacting the body portion and blocking rotation of the connector beyond a range of rotation.

The method can further comprise limiting rotation of the connector about the post, the body portion contacting the mask body and blocking rotation of the connector beyond a range of rotation.

The body portion can limit the range of rotation of the connector about the post to 90 degrees or less.

The method can further comprise restricting rotation of the connector within the opening via at least one stop bump positioned adjacent to the post along an extent of the opening, the stop bump contacting and blocking rotation of the connector to prevent the hook portion from rotating and detaching from the post.

The at least one stop bump can limit the range of rotation of the connector about the post to 90 degrees or less.

BRIEF DESCRIPTION OF THE DRAWINGS

Embodiments of the invention will now be described, by way of example only, with reference to the accompanying drawings in which.

DETAILED DESCRIPTION

As used herein the term 'over-molded' may be used to refer to any injection molding process, such as co-molding or two-shot molding, that combines two or more separate materials to create a single part, wherein the separate materials are permanently bonded to each other.

Figure 1:
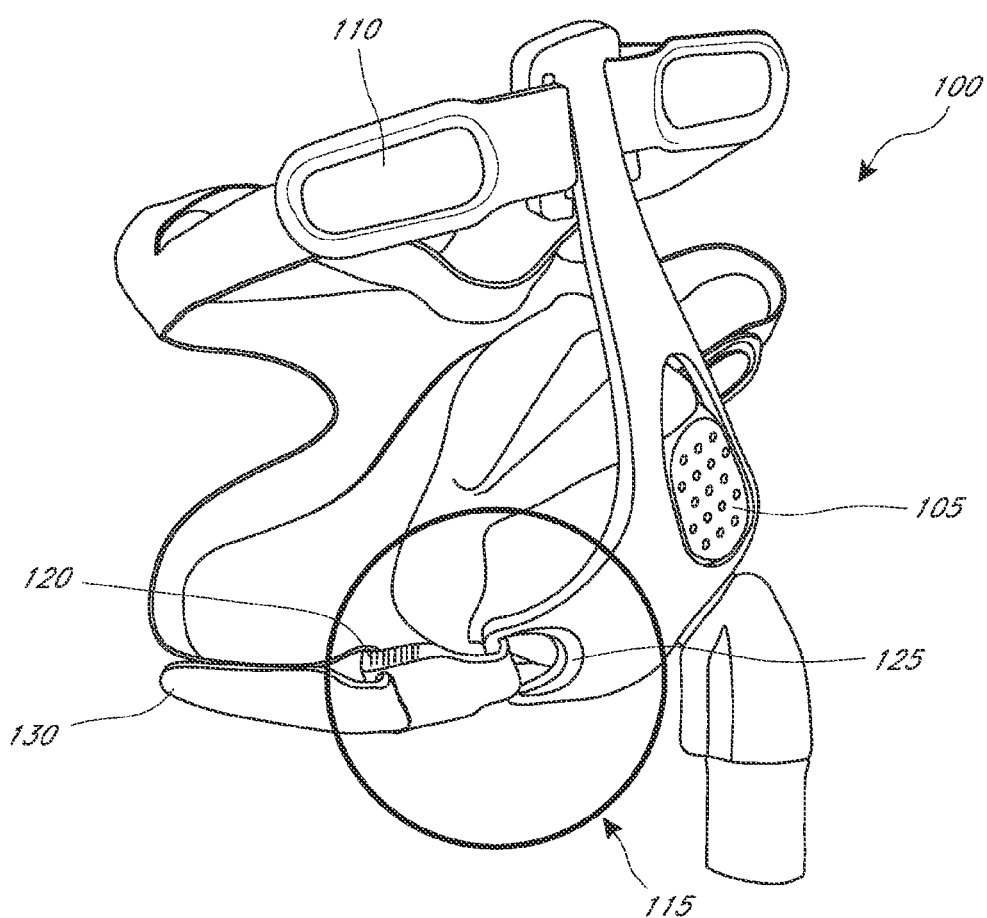
FIG. 1 shows a perspective view of a respiratory mask.

FIG. 1 shows a perspective view of a respiratory mask 100 comprising a mask body 105, a headgear 110 and a headgear connection assembly 115. The headgear connection assembly 115 is configured to provide a means of easily connecting and disconnecting at least a portion of the headgear 110 to the mask body 105. The headgear connection assembly 115 includes a clip 120 and a clip attachment portion 125, wherein the clip 120 is configured to provide a connection between a headgear strap 130 and the clip attachment portion 125. The clip attachment portion 125 can be defined by, carried by or attached to a portion of the mask, such as the mask body 105.

Figure 2:
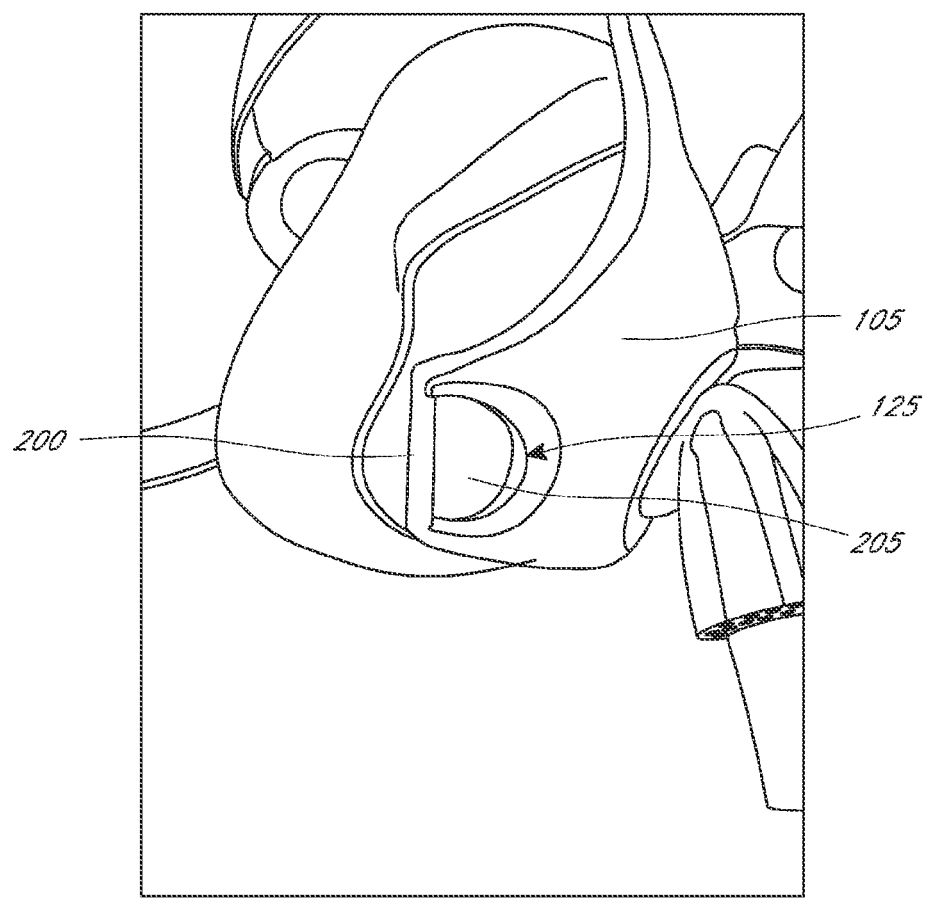
FIG. 2 shows a closer view of the clip attachment portion.

FIG. 2 shows the clip attachment portion 125. As shown, the clip attachment portion 125 is configured to be a part of the mask body 105. The clip attachment portion comprises a post 200 and a clip receiving opening 205. The post 200 is generally vertical, with respect to the orientation of the mask in use, when the user is sitting upright. However, the post 200 is not limited to a vertical position and may be oriented at various angles with respect to the orientation of the mask in use. The clip receiving opening 205 is forward of the post 200 (i.e., in a direction away from the user) and/or laterally inward of the post 200 (i.e., in a direction toward a centerline of the mask 100. The post 200 provides a location for the clip 120 to attach or be retained to the mask body 105.

The post 200 may be cylindrical in geometry (i.e., a circular cross-sectional shape) to allow easy connection of the clip 120 to the post 200. The cylindrical geometry is also configured to allow rotation of the clip 120 around the post 200. The post 200 is not limited to a circular cross-sectional shape and may include elliptical, polygonal, or a combination of several shapes. The cross-sectional shape of the post 200, in combination with the shape of the clip 120, may be configured to allow only a range of rotation of the clip 120 or bias the clip 120 towards preferred angles of rotation with respect to the post 200, if desired. The clip receiving opening 205 provides an opening for at least a portion of the clip 120 to pass through the clip attachment portion 125 and connect or attach to the post 200. This is just one configuration that can enable a clip 120 to be attached to a mask body 105.

In another embodiment, the post 200 may be positioned or configured such that an opening 204 may be unnecessary. For example, the post 200 may be attached to the mask body but positioned a distance away from a surface of the mask body. The distance away from the mask body may provide clearance for the clip 120 to connect or attach to the post 200. Other variations on geometry may provide improved functionality and will be described herein.

Figure 3A:
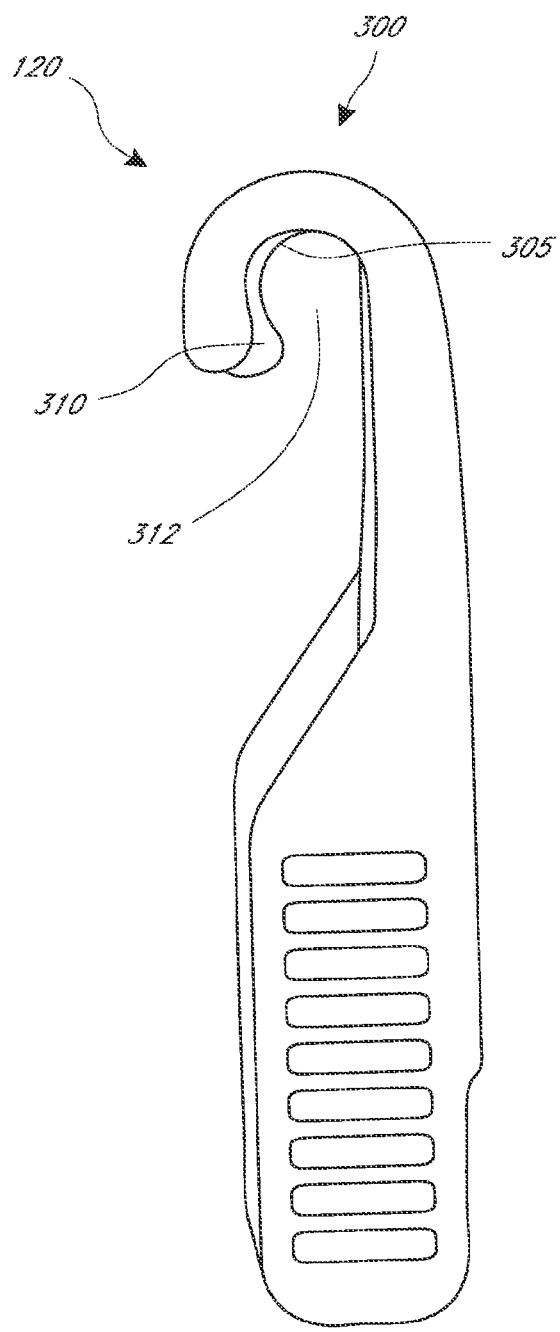
FIG. 3A shows a side view of the clip of the present disclosure.
Figure 3B:
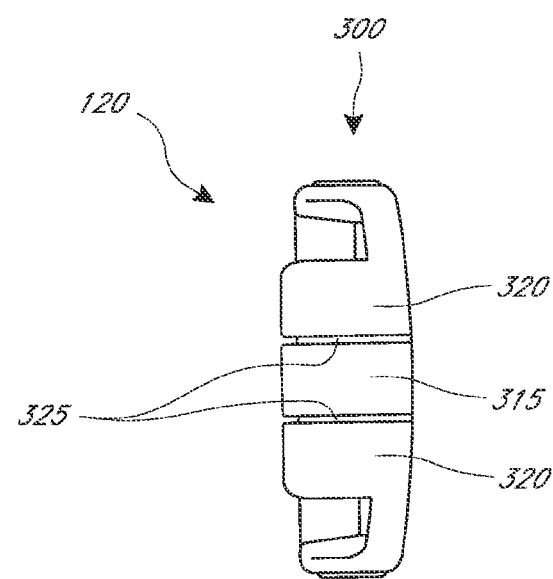
FIG. 3B shows a top view of the clip of the present disclosure.
Figure 3C:
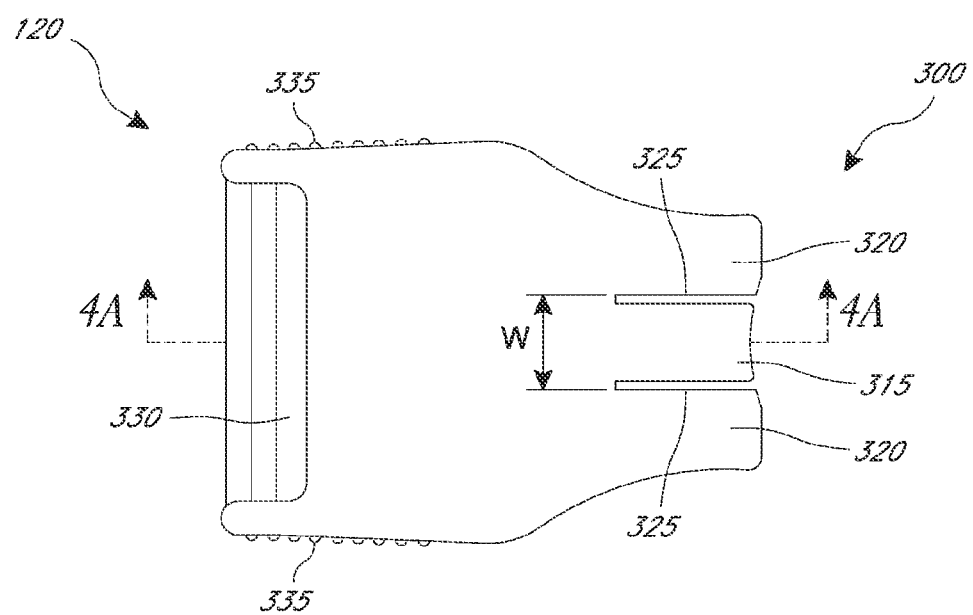
FIG. 3C shows a front view of the clip of the present disclosure.

FIGS. 3A-3C show a non-limiting exemplary embodiment of the clip 120. As shown, the clip 120 includes a hook 300, an interference bump 310, a central portion 315 and two outer portions 320, a headgear attachment loop 330 and one or more finger grips 335. The hook 300 is configured to fit around and attach to the corresponding post 200 of the clip attachment portion 125. The hook 300 can have a first leg portion and a second leg portion defining a U-shape or J-shape in cross-section, for example, to define a space for receiving the post 200. The first leg can be attached to the body portion of the clip 120 and the second leg can define a free end of the hook 300. In some configurations, the cross-sectional shape of the hook 300 can allow the hook 300 to wrap around a majority of post 200. However, the hook 300 is not limited to any specific cross-sectional shape. The hook 300 includes an inner surface 305, which can be configured to be at least partially cylindrical to match the cylindrical geometry of the post 200. The inner surface 305 is not limited to a partial cylindrical shape and may interface with the corresponding shape of the post 200.

At the end of the hook 300, the inner surface 305 can be connected to and/or merge into an interference bump 310 that is configured to narrow the hook entrance 312 relative to the diameter of the post 200. When attaching the hook 300 to the post 200, the hook 300 transitions from an undeflected state to a deflected state. In other words, the narrower hook entrance 312 created by the interference bump 310 requires the hook 300 to deflect outward in a direction away from the post 200 in order to widen the hook entrance 312 as the post 200 passes through the hook entrance 312. When the post 200 has fully passed through the hook entrance 312 and the clip 120 and the clip attachment portion 125 are connected, the hook 300 transitions back toward or to the undeflected state and the hook entrance 312 narrows. The interference bump 310 can act as a stop that retains the clip 120 on the post 200 by inhibiting or preventing the post 200 from passing through the hook entrance 312 in response to relatively low forces, such as those typically encountered during normal use, but that allows deliberate disconnection.

Further, in at least some configurations, the interference bump 310 may contact the post 200 to provide an interference fit between the post 200 and the clip attachment portion 125 when hook 300 is attached to the post 200. In addition or in the alternative, the hook 300 may have an inner diameter smaller than a diameter of the post 200 such that the hook 300 may have an interference fit with post 200. Such arrangements can assist in retaining the clip 120 in a desired rotational position. However, an interference fit connection is not necessarily utilized in all embodiments. In some configurations, when the hook 300 is in an undeflected state, the inner surface 305 and the interference bump 310 may define a diameter that is larger than the diameter of the post 200. With such an arrangement, the narrower hook entrance 312 created by interference bump 310 inhibits or prevents the post 200 from exiting through the entrance 312, but the clip 120 might otherwise have a relatively loose fit on the post 200 to allow rotational and/or sliding movement of the clip 120 relative to the post 200.

In the embodiment of FIGS. 3A-3C, the interference bump 310 has a constant geometry that extends along the width of the central portion 315. In other embodiments, the geometry of the interference bump 310 may extend along the entire width of the hook 300. Further, the geometry of the interference bump 310 and may be constant or varied along the width of the central portion 315 and/or the entire width of the hook 300.

The clip 120 can be made from a substantially rigid material, such as, but not limited to, polypropylene, nylon or polycarbonate. This material selection will provide the clip 120 with the structural integrity to support at least normal or expected retention forces applied by the headgear 110 to the mask body 105. The material can be capable of some elastic deformation so that the hook 300 can deflect when being attached to the post 200.

FIGS. 3B and 3C show an end view and a plan view, respectively, of the clip 120. It can be seen that the hook 300 comprises a central portion 315 and two outer portions 320. The central and outer portions 315, 320 can be configured to flex independently of each other. In one non-limiting exemplary embodiment, the central and outer portions are at least partially separated by one or more slots 325 (see also FIG. 5B). In the embodiment shown, the slots 325 extend through both sides of the U-shaped hook 300, however, the length of the slots may be varied to provide a level of flexibility that enables an easy connection between the clip 120 and the clip attachment portion 125 whilst reducing or eliminating the likelihood of unwanted disconnection during use.

Figure 4A:
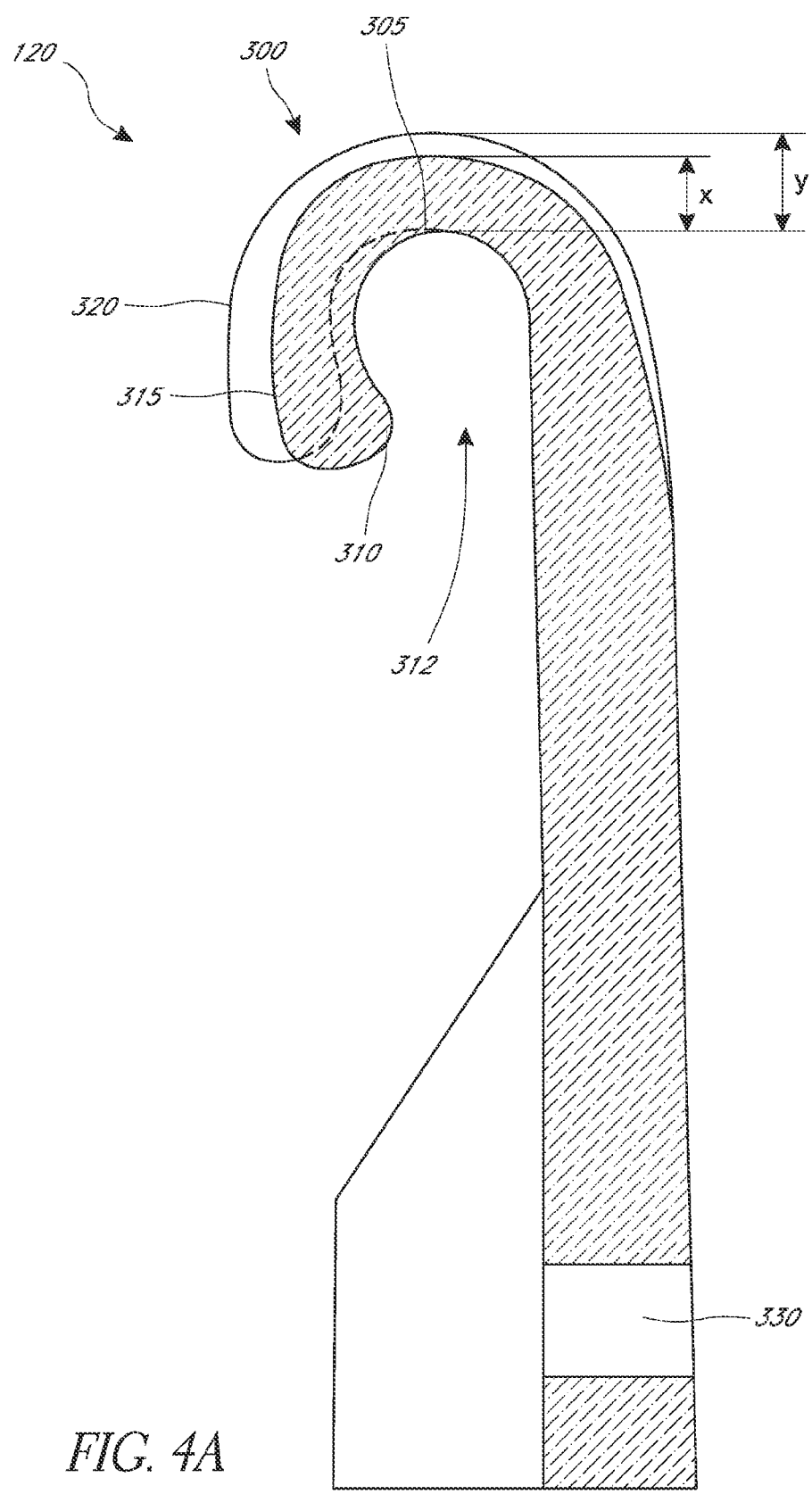
FIG. 4A shows a cross-sectional view of the clip of the present disclosure.
Figure 4B:
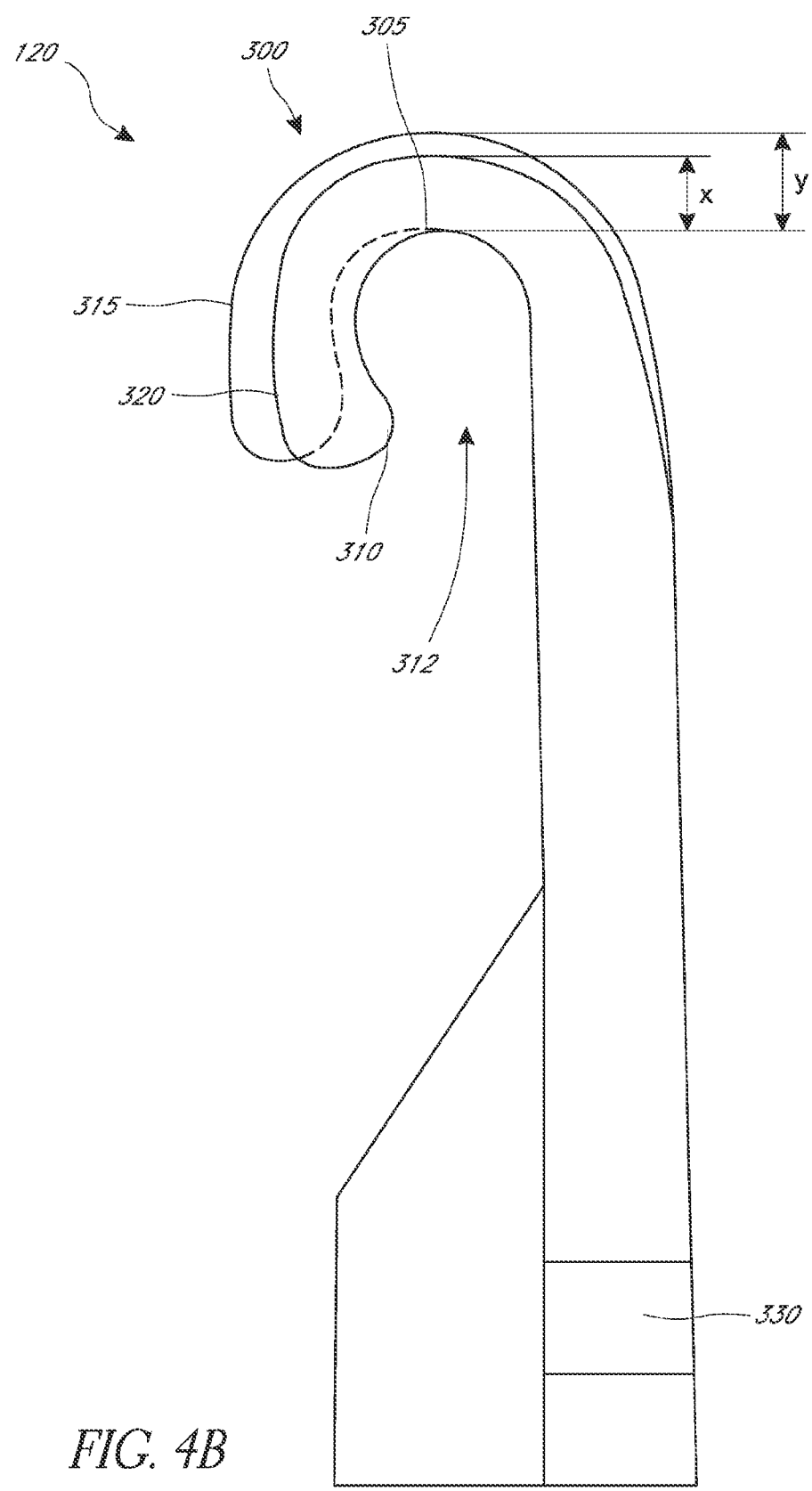
FIG. 4B shows a side view of the clip of the present disclosure.

FIG. 4A shows a cross-sectional view of the clip 120 along a line 4A-4A in FIG. 3C. This view shows that, in one non-limiting exemplary embodiment, the interference bump 310 can be more pronounced or only located on the central portion 315 (see also FIG. 3A). As a result of the interference bump 310 reducing the size of the hook entrance 312 to a size that is narrower than the diameter of the post 200, the central portion 315 may be configured to be more flexible than the outer portions 320 in order to deflect and allow the post 200 to move past the interference bump 310. A portion or an entire length of the central portion 315 of the hook 300 may have a reduced cross-sectional thickness x, in comparison to corresponding locations of the outer portions 320, which have a thickness of y. The reduced thickness may result in increased flexibility in the central portion 315, which may allow it to deflect more readily when passing over the post 200, thus improving ease of use. Alternatively, the width W, as shown in FIG. 3C, of the central portion 315 may be defined to provide the desired level of flexibility. The relatively thicker outer portions 320 can be more rigid or stronger than the central portion 315 and can accommodate or can be capable of accommodating a majority or a substantial entirety of the tension force of the headgear 110. In some configurations, the portions 315 and 320 can have the same or approximately the same thickness. In some configurations, the outer portions 320 may not flex or may not be required to flex to allow the post 200 to enter the space of the hook 300 through the entrance 312. The illustrated arrangement can also be reversed and the outer portions 320 can be thinner than the central portion 315 and/or can have interference bumps 310, as shown in FIG. 4B. In such arrangements, the outer portions 320 can flex and the central portion 315 may not flex or may not be required to flex for the post 200 to enter the space of the hook 300 through the entrance 312. Moreover, the entire arrangement can be reversed between the clip 120 and the mask body 105 such that the post 200 is defined or carried by the clip 120 and the hook 300 is defined or carried by the mask body 105.

Figure 5A:
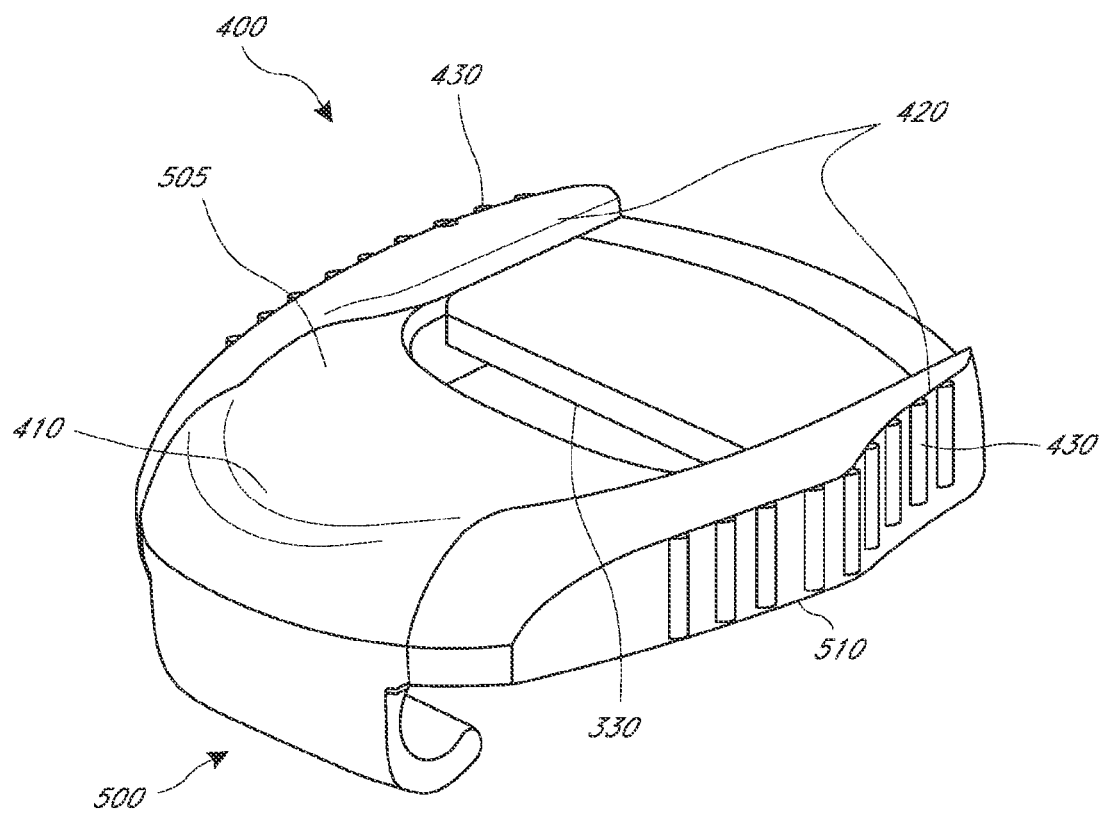
FIG. 5A shows a perspective view of a second embodiment of the clip of the present disclosure.

In another non-limiting exemplary embodiment, as shown in FIG. 5A, a clip 400 can comprise a substrate 410 and one or more over-molded portions 420. The substrate 410 can comprise the functional features of the clip being the hook 300 and headgear attachment loop 330. The substrate 410 can be made from a substantially rigid material as per the clip 120 of the previous embodiments. The over-molded portions 420 can be made from a soft and/or flexible material, such as, but not limited to, silicone rubber or a thermoplastic elastomer. The over-molded portions 420 can be configured to provide finger grips 430 on the sides of the clip 400. The finger grips 430 may be non-slip and comfortable to hold.

Figure 5B:
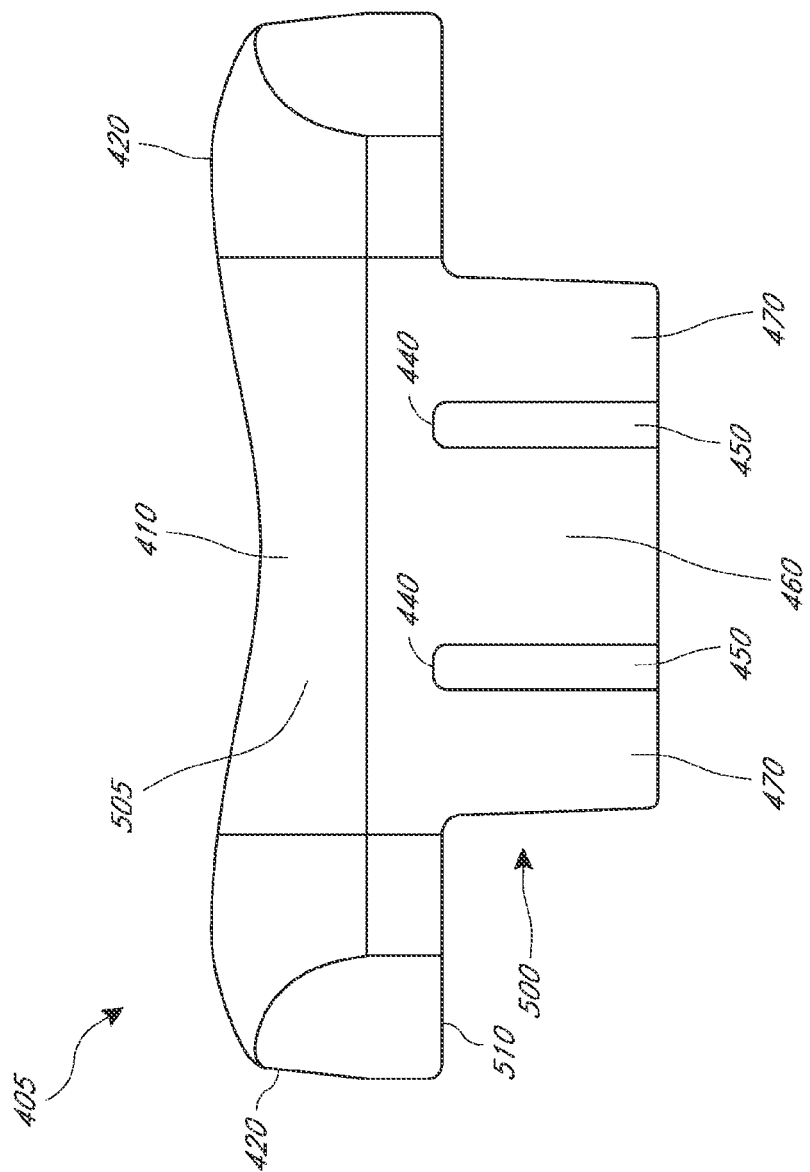
FIG. 5B shows an end view of a variation of the second embodiment of the clip of the present disclosure.

In a further variation of this embodiment, shown in FIG. 5B, the hook 500 of the substrate 410 includes slots 440. The slots 440 can be configured to provide flexibility to the hook 500 in the same way that the slots 325 have been previously described. In this embodiment, the slots 440 can also be configured to be filled with over-molded filler 450. The over-molded filler 450 can be configured to be bonded to the surfaces of the slots 440, thus providing a webbing-like structure between the central and outer portions 460 and 470 of the hook. The over-molded filler 450 can be made from a soft, flexible material that has at least some elasticity, such as silicone rubber or a thermoplastic elastomer; in some embodiments, the over-molded portions 420 and the over-molded filler 450 can be the same material. The flexible over-molded filler 450 allows the hook 500 to maintain the flexibility provided by the slots 440 whilst providing additional strength.

In an alternative embodiment (not shown), the outer portions 470 of the hook 500 may be created by an over-molding process. The outer portions 470 may have substantially the same geometry as the central portion 460 and be made of a material substantially the same as that described in relation to the over-molded filler 450. The over-molded outer portions 470 can provide increased flexibility during attachment of the clip as a result of the more flexible material.

Figure 6A:
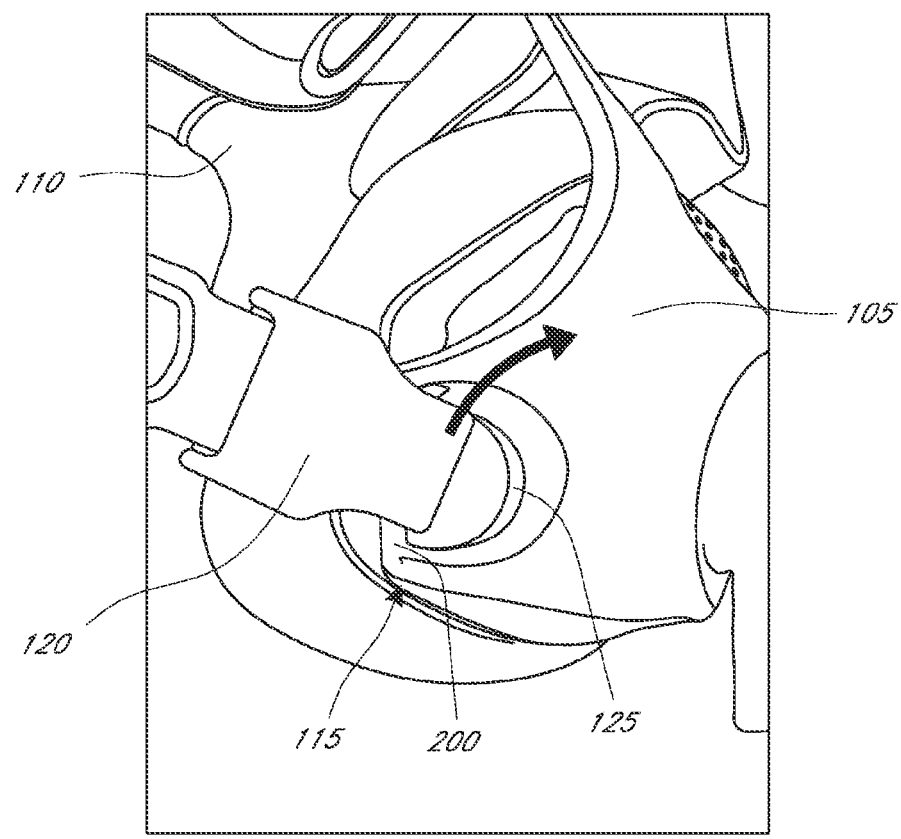
FIG. 6A shows a perspective view of the respiratory mask of FIG. 2, with the headgear connection assembly shown in close up.

FIG. 6A demonstrates one of the modes of separation that can occur in conventional hook and post attachment configurations. The clip 120 can rotate upwards off the post 200 (i.e., in the direction indicated by the arrow). This rotation can occur when there is an upwards force applied to the headgear which causes the clip 120 to rotate and an upper portion of the clip 120 to rotate away from the post 200. This can occur when a user moves his/her head whilst lying down or during fitting and adjustment of the mask. The upwards force and rotation of the clip 120 can result in the headgear 110 becoming detached from the mask body 105. Disconnection of the headgear during use of the mask can result in a loss of therapy for the user.

Figure 6B:
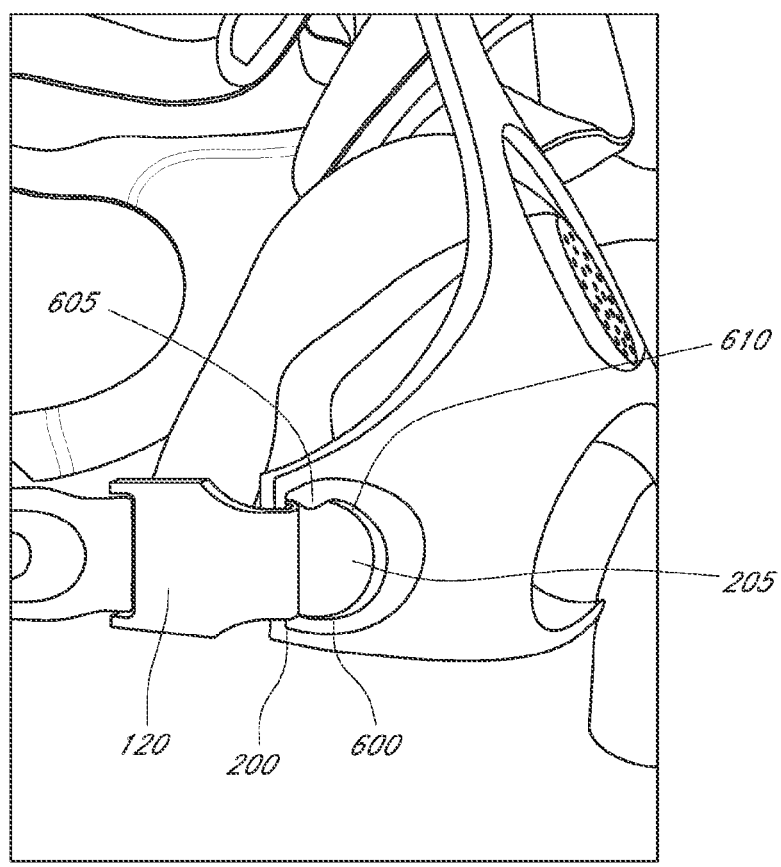
FIG. 6B shows a perspective view of mask embodiment that includes a stop bump.

FIG. 6B shows a non-limiting exemplary embodiment of a clip attachment portion 600 configured to address the aforementioned mode of separation. It can be seen that clip attachment portion 600 can be configured to include a stop bump 605 on its upper surface 610 (with respect to the orientation of the mask in use) when the user is sitting upright. The stop bump 605 is configured to be positioned adjacent to the post 200 and having a peak (lowermost point or portion) just forward of the clip 120 (i.e., away from the user) when the clip 120 is attached to the post 200. This positioning is such that, when an upwards force is applied to the headgear or clip 120, the clip 120 will come into contact with the stop bump 605 to stop rotation of clip 120. This will limit any further rotation and reduce or minimize the likelihood of the clip 120 becoming detached from the post 200. In at least some configurations, such an arrangement still permits movement of the clip 120 along the longitudinal axis of the post 200. In at least some configurations, the stop bump 605 can permit downward rotation of the clip 120 to permit disconnection of the clip 120 from the post 200.

The geometry of the stop bump 605 can be configured such that it does not impede the ability of a user to connect the clip 120 to the clip attachment portion 600. This is achieved by the stop bump 605 not extending too far into the clip receiving opening 205. The stop bump 605 may extend into the clip receiving opening 205 a distance that is close to, equal to or greater than a difference between the width of the clip receiving opening 205 along the direction parallel to an axis of the post 200 and the width of the clip 120 along a direction parallel to the axis of the post 200 when the clip 120 is connected to the post 200. Further, the stop bump 605 is depicted as a rounded convex protrusion extending into the opening 205. However, the stop bump 605 is not limited to any particular shape.

In further embodiments, there may be different stop bump 605 configurations. In one possible configuration, there may be more than one stop bump 605 in each clip attachment portion 600. For instance, there may be stop bumps 605 on both the upper and lower surfaces of the clip attachment portion 600. Each stop bump 605 may have a different size, shape and position to inhibit, limit or prevent rotation of the clip 120 while still allowing the clip 120 to be attached to the post 200. In some configurations, vertical movement of the clip 120 along the longitudinal axis of the post 200 is permitted. In another configuration, there may be a single stop bump 605 located on the lower surface of the clip attachment portion 600.

Figure 7:
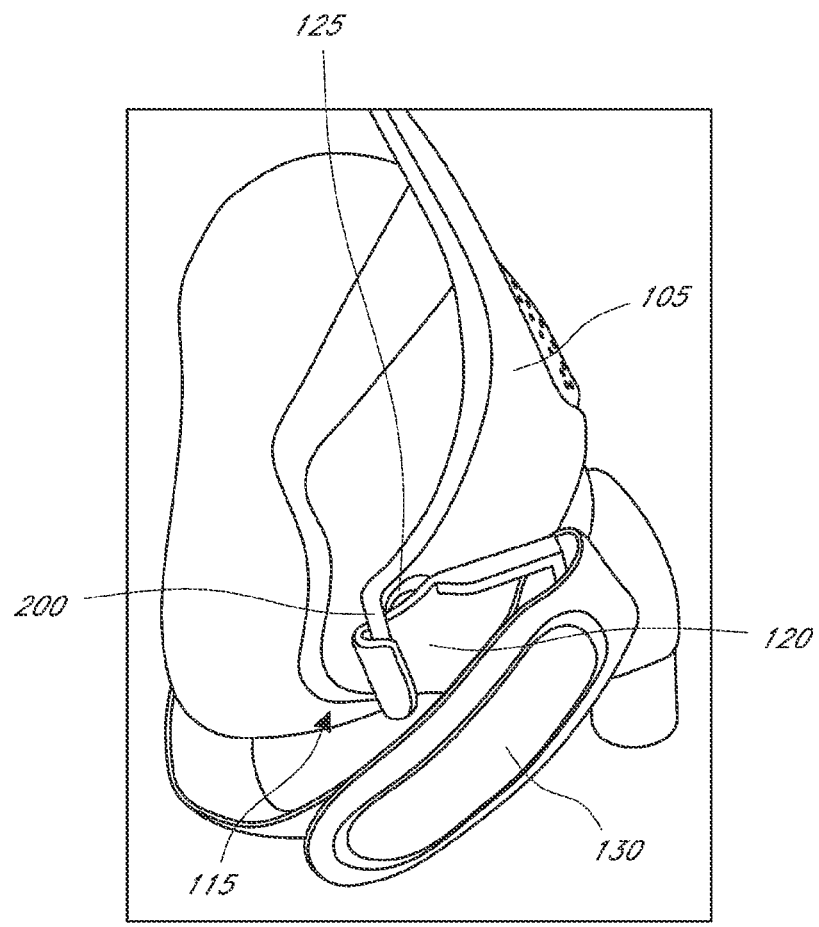
FIG. 7 shows a perspective view of the respiratory mask of FIG. 2, with the headgear connection assembly shown in a different position.

A further orientation of the clip 120 relative to the clip attachment portion 125 that can occur in conventional hook and post attachment configurations is shown in FIG. 7. It can be seen that the clip 120 has been over-rotated on the post 200 such that it is directed in the opposite direction to which headgear retention forces need to be applied (i.e., away from the user). Over-rotation of the clip 120 on the post 200, which can occur for example when the mask 100 is not fitted to a user, can make it difficult to fit the mask 100, as the headgear 110 may lose its shape and the headgear straps 130 may tangle. Over-rotation of the clip 120 may also reduce the circumference of the headgear 110 and mask body 105 loop, thereby making the headgear 110 too small for the user and, thus, difficult to fit.

Figure 8:
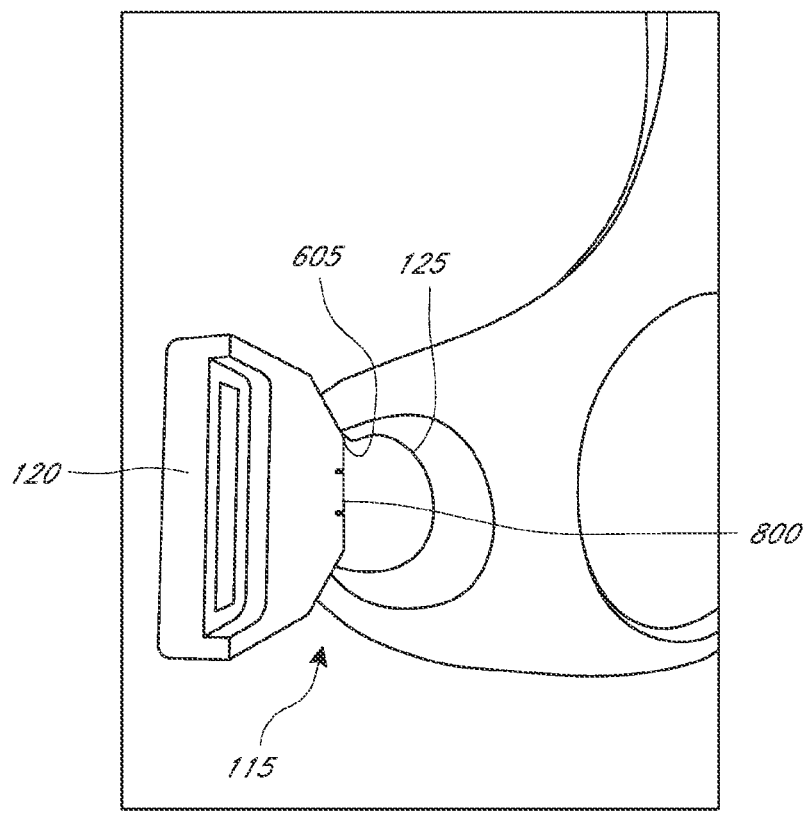
FIG. 8 shows a close up perspective view of a headgear connection embodiment that includes a stop bump and the first clip embodiment.

As shown in FIG. 8, the stop bump 605 as described in relation to FIG. 6B may be configured to limit rotation of the clip 120 on the post 200. During rotation of the clip 120 on the post 200, a surface 800 of the clip 120, such as an outer and/or upper surface, can come into contact with the stop bump 605, which may limit, inhibit or prevent any further rotation of the clip 120 on the post 200. In a preferred embodiment, the clip 120 and the stop bump 605 can be designed such that a maximum angle of rotation R may be up to approximately 90° relative to a normal position of the clip 120 during use of the mask 100. In other words, a maximum range of rotation of the clip 120 on the post 200 may be limited to approximately 90° relative to a normal position of the clip 120 during use of the mask 100. The size, shape and position of the stop bump 605 may be varied to vary the range of rotation of the clip 120 on the post 200.

Figure 9A:
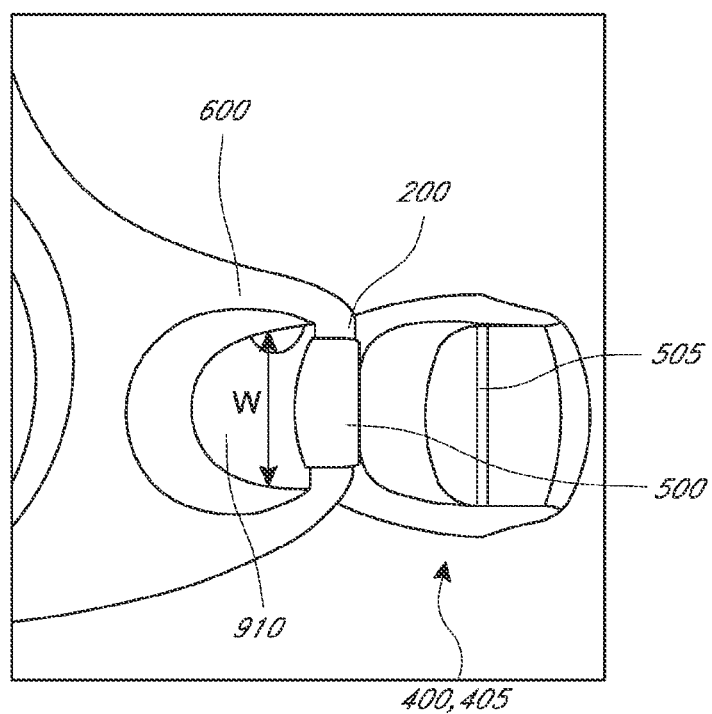
FIG. 9A shows a close up rear view of a clip attachment embodiment including the second clip embodiment.
Figure 9B:
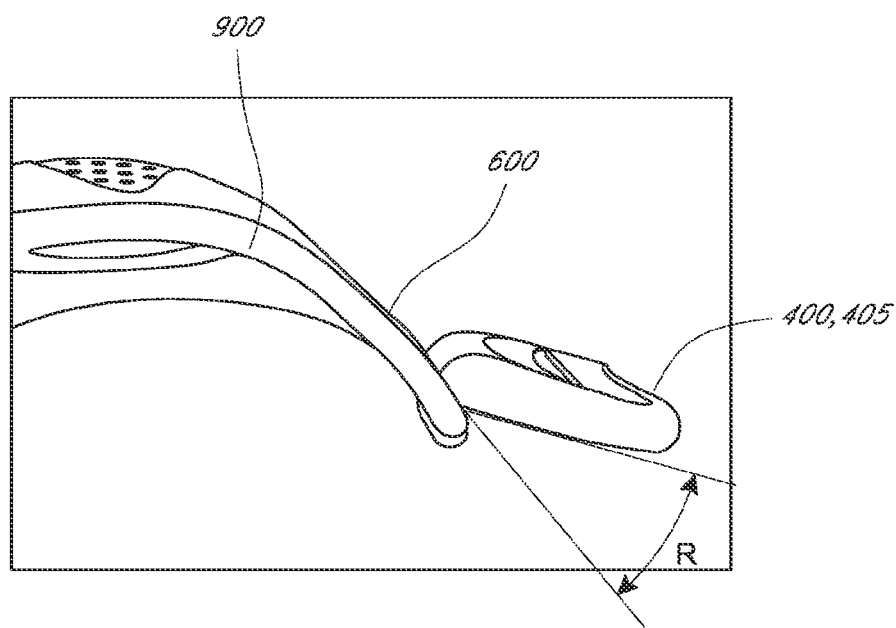
FIG. 9B shows a plan view of a clip attachment embodiment including the second clip embodiment.

The clip embodiment of FIGS. 5A and 5B provides an alternative non-limiting exemplary embodiment that may restrict or minimize over-rotation of the clip 120. The hook 500 extends from a lower surface 510 of the clip body 505 at or near one end. The hook is substantially narrower than the clip body. FIG. 9A shows a rear view of the clip 400 or 405 attached to a clip attachment portion 600. It can be seen that at least a portion of the clip body 505 is substantially the same width or, preferably, wider than the width W of the clip receiving opening 910. The width of the hook 500 can be less than at least a portion of the body 505 such that the hook 500 can pass through a clip receiving opening 910 of the clip attachment portion 600 to attach to a post 200. The clip body 505 width allows it to come into contact with the clip attachment portion 600 before rotating too far, as shown in FIG. 9B. FIG. 9B shows the clip 400 or 405 attached to a mask frame 900 viewed from above. The clip is rotated until the clip body contacts the clip attachment portion 600 and cannot rotate any further. In a preferred embodiment, the width of the clip body 505 and the width W of the clip receiving opening 910 can be designed such that the maximum angle of rotation R may be up to approximately 90° relative to a normal position of the clip 120 during use of the mask 100. In other embodiments, more or less rotation may be desirable. In alternative embodiments, there may be a bump or other suitable geometry on the clip 400 or 500 that limits rotation rather than width of the clip body 505. Even further, the clip embodiment of FIGS. 5A and 5B may also be combined with a stop bump on an upper surface 610 of the clip attachment portion 600, as shown in FIG. 9A. When the clip body 505 is rotated on the post 200, the clip body 505 may contact the stop bump 605 to limit rotation of the clip body 505.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A mask assembly comprising:
   a mask body;
   an attachment portion disposed on the mask body, the attachment portion comprising;
   an opening;
   a post disposed along an outer edge of the opening; and
   one or more limitation bumps positioned adjacent to the post on a surface of the opening, the one or more limitation bumps extending into the opening;
   wherein the one or more limitation bumps are configured to limit or block rotation of a cooperating portion of the mask assembly relative to the post.

2. The mask assembly of claim 1, wherein the one or more limitation bumps limits one or both of rotation about an axis of the post and rotation normal to the axis of the post.

3. The mask assembly of claim 1, wherein at least one of the one or more limitation bumps are located on an upper edge of the opening.

4. The mask assembly of claim 1, wherein the post is generally vertical relative to an orientation of the mask body in use when a user is sitting upright.

5. The mask assembly of claim 1, wherein the opening is laterally inward of the post.

6. The mask assembly of claim 1, wherein the post has a polygonal cross-sectional shape.

7. The mask assembly of claim 1, wherein a cross-sectional shape of the post is configured to limit a range of rotation of the cooperating portion.

8. The mask assembly of claim 1, wherein the one or more limitation bumps have a rounded convex protrusion extending into the opening.

9. The mask assembly of claim 1, wherein the one or more limitation bumps include a first limitation bump and a second limitation bump, wherein the first limitation bump is positioned on an upper surface of the opening, wherein the second limitation bump is positioned on a lower surface of the opening.

10. The mask assembly of claim 1, wherein the first limitation bump is a different size or shape than the second limitation bump.

11. The mask assembly of claim 1, wherein a range of rotation of the cooperating portion of the mask assembly relative to the post is 90 degrees or less.

12. The mask assembly of claim 1, wherein the post has a cylindrical cross-sectional shape.

13. The mask assembly of claim 1, wherein the one or more limitation bumps are configured to extend partially into the opening to allow for the cooperating portion to connect to the post.

14. The mask assembly of claim 1, wherein the one or more limitation bumps is a single limitation bump, wherein the single limitation bump is located on an upper side of the opening and limits upward rotation of the cooperating portion of the mask assembly relative to the post.

* * * * *